(12) United States Patent
Murakami

(10) Patent No.: US 8,236,257 B2
(45) Date of Patent: Aug. 7, 2012

(54) BIOLOGICAL COMPONENT-MEASURING DEVICE AND METHOD FOR CALIBRATING THE SAME

(75) Inventor: Motoaki Murakami, Makinohara (JP)

(73) Assignee: Nikkiso Co., Ltd., Tokyo (JP)

(\*) Notice: Subject to any disclaimer, the term of this patent is extended or adjusted under 35 U.S.C. 154(b) by 957 days.

(21) Appl. No.: 12/298,523

(22) PCT Filed: Apr. 26, 2007

(86) PCT No.: PCT/JP2007/000466
§ 371 (c)(1),
(2), (4) Date: Oct. 24, 2008

(87) PCT Pub. No.: WO2007/129463
PCT Pub. Date: Nov. 15, 2007

(65) Prior Publication Data
US 2011/0198241 A1    Aug. 18, 2011

(30) Foreign Application Priority Data
Apr. 26, 2006    (JP) .................................. 2006-122469

(51) Int. Cl.
*B01L 99/00* (2010.01)
*G01N 27/403* (2006.01)

(52) U.S. Cl. .................... 422/509; 422/503; 204/409

(58) Field of Classification Search .................. 422/50, 422/401, 68.1, 502–505, 509, 510, 82.01–82.03; 204/409–412
See application file for complete search history.

(56) References Cited

U.S. PATENT DOCUMENTS
| 4,202,747 A | * | 5/1980 | Buzza et al. .................. 204/411 |
| 4,871,439 A | * | 10/1989 | Enzer et al. ................... 204/401 |
| 5,118,473 A | * | 6/1992 | Coleman et al. ............. 422/68.1 |

FOREIGN PATENT DOCUMENTS
| JP | 52-135795 A | 11/1977 |
| JP | 54-82885 A | 7/1979 |
| JP | 55-21905 A | 2/1980 |
| JP | 56-28765 A | 3/1981 |
| JP | 58-152537 A | 9/1983 |

(Continued)

OTHER PUBLICATIONS

Full English language translation of JP 3-12134 A (Terumo Corp.) patent published Jan. 21, 1991.*

(Continued)

*Primary Examiner* — Alex Noguerola
(74) *Attorney, Agent, or Firm* — McDermott Will & Emery LLP

(57) ABSTRACT

This invention provides a biological component-measuring device, enabling the operator to easily calibrate the entire device and capable of measuring biological components accurately, and a method for calibrating the device. The device measures a sample including a body fluid taken through a body fluid sampler by sending it with a pump through a sample channel to a sensor. The device further includes a calibrating liquid channel through which a calibrating liquid can be supplied to the sensor via the sample channel by a switching of a first flow path changeover valve placed in the sample channel at a location upstream of the pump and connected to the channel. The method includes introducing the calibrating liquid in the calibrating liquid channel, via other channels, into the sensor by switching the valve.

10 Claims, 6 Drawing Sheets

FOREIGN PATENT DOCUMENTS

| | | |
|---|---|---|
| JP | 58-198351 A | 11/1983 |
| JP | 62-1603 U | 1/1987 |
| JP | 03-12134 A | 1/1991 |
| JP | 03-178641 A | 8/1991 |
| JP | 2003-107080 A | 4/2003 |
| JP | 2005-237938 A | 9/2005 |
| JP | 2006-130306 A | 5/2006 |

OTHER PUBLICATIONS

Full English language transation of JP 3-178641 A (Terumo Corp.) patent published Aug. 2, 1991.*

JPO computer-generated English language translation of the claims and Detailed Description of JP 2003-107080 A (Jun Kikuchi) patent published Apr. 9, 2003.*

JPO computer-generated English language translation of the claims and Detailed Description of JP 2005-237938 A (Hiroki Ogawa), patent published Sep. 8, 2005.*

JPO computer-generated English language translation of the claims and Detailed Description of JP 2006-130306 A (Nikkiso Co., Ltd.), patent published May 25, 2006.*

* cited by examiner

BIOLOGICAL COMPONENT-MEASURING DEVICE AND METHOD FOR CALIBRATING THE SAME

CROSS-REFERENCE TO PRIOR RELATED APPLICATIONS

This is a U.S. National Phase Application under 35 U.S.C. §371 of International Patent Application No. PCT/JP2007/000466 filed Apr. 26, 2007 which claims the benefit of Japanese Application No. 2006-122469 filed Apr. 26, 2006 both of which are incorporated by reference herein in their entireties.

BACKGROUND OF THE INVENTION

1. Field of the Invention

The present invention relates to a biological component-measuring device and a method for calibrating a biological component-measuring device. More particularly, the present invention relates to a hygienic biological component-measuring device that is used for medical support devices and devices of this kind, which biological component-measuring device enables the operator to easily calibrate the entire device as well as the sensors thereof, and to attach a channel-carrying substrate to the device easily, which improves operability. The present invention also relates to a method for calibrating a biological component-measuring device, by which method the operator is able to calibrate the entire device easily while a biological component of a patient is being measured.

2. Description of the Related Art

An example of the biological component-measuring devices that have been conventionally used in the hospital is a glucose-measuring device by which the blood sugar level of a blood sample is measured. An example of the medical devices with a glucose-measuring device incorporated is an artificial endocrine pancreas device. Among the artificial endocrine pancreas devices, a type of artificial endocrine pancreas device that carries out a closed-loop control where components in the blood, which is a body fluid, of a patient, such as glucose, are measured continuously or at intervals, and liquid medicines such as glucose or insulin are injected into the patient based on the measurement in order to control the patient's conditions, requires accurate and safe operation during its use, often over a long period of time. Specifically, it is said that an artificial endocrine pancreas device should be capable of providing accurate measurement for a period from about four hours to about one week. It is very important for keeping the artificial endocrine device safe to periodically calibrate the sensors to obtain accurate and invariable measured values, and to calculate the amount of a liquid medicine necessary to be injected into the patient.

The glucose sensor sometimes outputs inaccurate values, which is caused by variation with time in the tubes passing through a peristaltic pump that is placed in various channels in an artificial endocrine pancreas device, which channels are also called tubes because they are typically made of soft and elastic tubes, especially in the tubes through which sampled blood is sent to the glucose sensor. The output of inaccurate values may also be caused by variation with time in the sensor per se; the output data or measured values themselves are inaccurate.

Therefore, the sensor of a conventional artificial endocrine pancreas device is periodically calibrated, which involves temporary stopping of sampling blood from the patient or injecting a liquid medicine into him/her. Specifically, for example, an indwelling needle kept in a vein of a patient is taken away from him/her and the artificial endocrine pancreas device is removed from him/her. Then, the sensors of the device are calibrated. After the completion of the calibration, the indwelling needle is inserted to his/her vein and kept in it again, which is followed by measurement of the blood sugar level of him/her with the artificial endocrine pancreas device. The measurement provides a value of the blood sugar level, based on which an amount of a liquid medicine is decided, and the liquid medicine in the amount is injected into him/her.

JP 58-152537 A discloses an invention for a blood substance-monitoring device that continuously measures substances in blood, which is an example of a biological component-measuring device whose sensors can be calibrated while sampling of body fluid of a patient is being continued. According to the invention, blood is continuously sampled through an indwelling cannula kept in a vein and substances included in the blood sample are measured. When the sensors are calibrated, the liquid to be sent to the sensors is switched from the blood sample to a calibrating liquid at a location just upstream of the sensors. After the completion of the calibration, the liquid to be sent to the sensors is immediately returned to the blood sample and the measurement is resumed. Blood being sampled during the calibration is disposed of through a waste liquid channel because the time period for the calibration is short. JP 52-135795 A teaches a method of calibrating sensors for glucose-measuring devices. This invention also employs the idea of switching liquids to be sent to the sensors. Specifically according to the invention, a calibrating liquid is introduced, by the switching, into the channel at a location near the sensors, downstream of a pump placed in the channel through which the blood sample is transferred. There are other relevant inventions. JP 58-198351A discloses a method of measuring a specified component of the body fluid while a sample of the body fluid, such as blood, is being diluted several different times. JP 54-82885 A, JP 55-21905 A, and JP 56-28765 A disclose blood sugar level-controlling devices that employ a specified method of controlling the amount of insulin to be injected based on values obtained by continuous measurement of blood sugar level, and artificial endocrine pancreas devices.

SUMMARY OF THE INVENTION

The biological component-measuring devices mentioned hereinbefore are advantageous because sensors are calibrated easily and quickly. However, calibration of only the sensors of a biological component-measuring device sometimes is not sufficient to provide accurate measurement because of aging of or variation with time in other units and members of the device. In other words, variation with time in units and members of conventional biological component-measuring devices, other than the sensors thereof, brings variation in measured values. Calibrating the sensors only does not make variation in values measured by biological component-measuring devices avoidable, when the flow rate of a sample varies because of changes in pumps and/or sample channels, especially when the ratio of the amount of a sample to that of a diluent is changed.

An objective of the present invention is to provide a biological component-measuring device which is capable of removing the problems as described above and measuring biological components accurately, and the whole of which can be calibrated easily and thoroughly. Another objective of the present invention is to provide a biological component-measuring device, various channels of which can be exchanged hygienically and easily, and which is still capable of measuring biological components. A further objective of the present invention is to provide a safe, reliable and easy method for calibrating a biological component-measuring device.

In order to achieve the foregoing objectives, the present invention provides the following features.

A biological component-measuring device in which a sample including a body fluid taken by a body fluid sampler is transferred to a sensor through a sample channel by a pump and a biological component in the sample is measured by the sensor, which includes:

a first flow path changeover valve placed in the sample channel at a location upstream of the pump; and a calibrating liquid channel connected to the first flow path changeover valve, capable of supplying a calibrating liquid to the sensor through the sample channel by a switching operation of the first flow path changeover valve.

The biological component-measuring device further includes a body fluid-diluting liquid channel for supplying a body fluid-diluting liquid to the body fluid sampler.

The biological component-measuring device further includes:

a second flow path changeover valve placed in the body fluid-diluting liquid channel; and a second body fluid-diluting liquid channel, connected to the second flow path changeover valve, capable of mixing the body fluid-diluting liquid in the body fluid-diluting liquid channel with the calibrating liquid by a switching operation of the second flow path changeover valve.

The biological component-measuring device further includes a flushing liquid channel through which a flushing liquid flows, the flushing liquid channel connected with the sample channel via a third flow path changeover valve at a location between the body fluid sampler and the first flow path changeover valve, and/or between the second flow path changeover valve and the body fluid sampler.

The flushing liquid of the biological component-measuring device further includes a predetermined concentration of biological components.

The biological component-measuring device further includes a first diluent channel through which a diluent for diluting the sample in the sample channel flows, the first diluent channel connected with the sample channel at a location downstream of the first flow path changeover valve.

The biological component-measuring device further includes a gas channel connected to the first diluent channel or a junction of the first diluent channel and the sample channel.

The biological component-measuring device further includes a channel-carrying substrate, in which a sample including a body fluid taken by a body fluid sampler is transferred to a sensor through a sample channel by a pump and a biological component in the sample is measured by the sensor, the channel-carrying substrate including:

a substrate detachably mountable on the biological component-measuring device proper;

a sample channel connectable to the body fluid sampler and the sensor for measuring a biological component in the sample including the body fluid taken by the body fluid sampler, the sample channel fixed to the substrate so as to be capable of transferring the sample to the sensor by the pump; and a calibrating liquid channel connectable to a calibrating liquid tank, and connected to the sample channel at a location upstream of the pump via a first flow path changeover valve, the calibrating liquid channel fixed to the substrate so as to be capable of supplying a calibrating liquid stored in the calibrating liquid tank to the sample channel.

The substrate of the biological component-measuring device further includes a body fluid-diluting liquid channel fixed thereto, connectable to a body fluid-diluting liquid tank, for supplying a body fluid-diluting liquid stored in the body fluid-diluting liquid tank to the body fluid sampler.

The biological component-measuring device further including includes:

a second flow path changeover valve placed in the body fluid-diluting liquid channel; and a second body fluid-diluting liquid channel, connected to the second flow path changeover valve, capable of mixing the body fluid-diluting liquid in the body fluid-diluting liquid channel with the calibrating liquid by a switching operation of the second flow path changeover valve.

The substrate of the biological component-measuring device further includes a flushing liquid channel through which a flushing liquid flows, the flushing liquid channel connectable to a flushing liquid tank and connected with the sample channel at a location between the body fluid sampler and the first flow path changeover valve, and/or between the second flow path changeover valve and the body fluid sampler.

The flushing liquid of the biological component-measuring device further includes a predetermined concentration of biological components.

The substrate of the biological component-measuring device further includes a first diluent channel through which a diluent for diluting the sample in the sample channel flows, the first diluent channel connectable to a diluent tank and connected with the sample channel at a location downstream of the first flow path changeover valve.

The substrate of the biological component-measuring device further includes a gas channel connected to the first diluent channel or a junction of the first diluent channel and the sample channel.

The calibrating liquid tank of the biological component-measuring device is placed at a lower level than the body fluid sampler.

The method of calibrating the biological component-measuring device includes transferring the calibrating liquid from the calibrating liquid channel to the sensor via the sample channel by a switching of the first flow path changeover valve.

The method of calibrating the biological component-measuring device further includes:

a first operation of carrying out a zero point calibration of the biological component-measuring device by supplying the diluent to the sample channel from the first diluent channel prior to sampling a biological component;

a second operation of supplying the flushing liquid to the sample channel while the biological component is being measured; and a third operation of introducing the calibrating liquid in the calibrating liquid channel into the sensor via the sample channel by a switching of the first flow path changeover valve, without introducing the flushing liquid into the sensor.

The method of calibrating the biological component-measuring device further includes:

a first operation of supplying a first portion of the flushing liquid at a first flow rate that is larger than a flow rate of the sample, to the sample channel from the flushing liquid channel while a biological component is being measured;

a second operation of introducing the calibrating liquid into the sensor by a switching of the first flow path changeover valve placed in the sample channel, after the first portion of the flushing liquid is introduced into the sample channel and the sensor; and a third operation of introducing a second portion of the flushing liquid at a flow rate smaller than the first flow rate into the sample channel at a location upstream of the first flow path changeover valve and into the body fluid sampler during the second operation, to prevent the body fluid from flowing into the part filled with the second portion of the flushing liquid.

The present invention employs the arrangement in which a calibrating liquid channel through which a calibrating liquid to correct measured values is supplied is connected to a sample channel via a first flow path changeover valve at a location upstream of a pump placed in the sample channel. This arrangement makes it possible not only to calibrate a sensor incorporated into the biological component-measuring device, but also to correct errors due to variation with time in other elements of the device such as the sample channel, the pump and the sensor, which enables the device to carry out accurate measurement at all times. Specifically, the sensor of the device sees variation with time in its output, and outputs and displays inaccurate measured values. The flow of a calibrating liquid through the elements clarifies a difference between the value currently outputted by the sensor and the value initially outputted by it. The biological component-measuring device is able to output accurate measured values by correcting outputs of the sensor accordingly after the calibration.

A biological component-measuring device, such as an artificial endocrine pancreas device, according to the present invention is provided with a body fluid-diluting liquid channel for supplying a body fluid-diluting liquid to a body fluid sampler. When a body fluid, such as blood, taken by the body fluid sampler is mixed with the body fluid-diluting liquid, components apt to coagulate in the body fluid such as blood may be prevented from coagulation while the sampled body fluid is being transferred through the sample channel to the sensor. The prevention of the body fluid such as blood from coagulation reduces, to an ignorable extent, variation in measured values due to blood clots developed, for example in the sample channel, compared with initially measured values outputted by the biological component-measuring device at the commencement of measurement. Therefore the present invention makes it possible to prevent a body fluid such as blood flowing through the sample channel from coagulating, and enables a sample made by diluting the body fluid with the body fluid-diluting liquid to flow through the sample channel smoothly. It is more preferable to prevent blood from coagulation, if the body fluid-diluting liquid includes an anticoagulant such as heparin. The present invention also provides a biological component-measuring device capable of reducing the amount of a sampled body fluid because the body fluid-diluting liquid is supplied to the body fluid sampler, and adjusting the concentration of a component to be measured to a concentration within such a range that the sensor is able to output the measured value properly.

The biological component-measuring device according to the present invention is provided with a second flow path changeover valve in the body fluid-diluting liquid channel, and the second flow path changeover valve is connected with a second body fluid-diluting liquid channel. When the second flow path changeover valve is switched, the body fluid-diluting liquid in the body fluid-diluting liquid channel is mixed with a calibrating liquid flowing in the calibrating liquid channel. Once the calibrating liquid is mixed with the body fluid-diluting liquid, a calibrating liquid diluted with the body fluid-diluting liquid flows through the sample channel and the sensor, which provides data for calibration obtained with the calibrating liquid in a concentration resulting from the dilution with the body fluid-diluting liquid. Therefore the present invention provides a biological component-measuring device, calibrated several times with calibrating liquids in different concentrations, capable of outputting accurately corrected measured values.

Furthermore, when the first flow path changeover valve and the second flow path changeover valve are switched simultaneously, the body fluid-diluting liquid is allowed to flow through the second body fluid-diluting liquid channel. Then, the body fluid-diluting liquid mixes with the calibrating liquid in the calibrating liquid channel, and the mixture liquid of the calibrating liquid and the body fluid-diluting liquid is transferred to the sensor through the first flow path changeover valve and the sample channel. This connection of the channels is able to correct variation in measured values outputted by the sensor, which variation is caused by variation with time in the discharge of the pump placed in the sample channel and in that of the pump transferring the body fluid-diluting liquid. When each of the pump for supplying the body fluid-diluting liquid to the body fluid-diluting liquid channel, and the pump for transferring a sample to the sample channel is a pump comprised of a tube made of an elastic material and a member for squeezing this tube such as a roller, examples of which may include rotary peristaltic pumps and linear peristaltic pumps, variation with time in the inner diameter of the tube causes another variation with time in the discharge amounts of the pumps. Such variation with time in measured values outputted by the sensor is corrected by the simultaneous switching of the first and second flow path changeover valves.

The present invention employs a flushing liquid channel connected to the sample channel at a location between the body fluid sampler and the first flow path changeover valve, and/or connected to a branch channel at a location between the body fluid sampler and the second flow path changeover valve that is so placed in the body fluid-diluting channel as to make the body fluid-diluting channel bifurcate, which enables a flushing liquid drawn through the flushing liquid channel to clean the elements such as the sample channel, the body fluid sampler, and the sensor and discharge undesired matters such as clots and gelled body fluid as well as the sample from the biological component-measuring device. Therefore if the sample channel, the body fluid sampler and the sensor are cleaned when or just before a calibration is started, coagulation and/or deterioration of a body fluid such as blood in the sample may be prevented and measurement may be resumed immediately after the calibration. Also, the introduction of the flushing liquid into the part of the sample channel that runs between the body fluid sampler and the first flow path changeover valve during a calibration will prevent coagulation of the body fluid such as blood.

Moreover, when the flushing liquid includes a predetermined amount of the measured component of the body fluid, the transference of this flushing liquid to the sensor provides a calibration of the sensor only. When only the sensor can be calibrated, variation with time in measured values due to variation with time in the sample channel and the pump placed in the sample channel can be detected. When the pump is composed of a part of the sample channel and a rotary peristaltic pump that squeezes the part, the operator may judge from the result of the detection that variation with time in the sample channel makes the measured values inaccurate. S/he may also judge easily that the sample channel should be changed to a new one.

A check valve should preferably be placed in the calibrating liquid channel at a location upstream of the first flow path changeover valve. When the calibrating liquid channel is provided with a check valve, it may prevent a sample taken by the body fluid sampler from flowing into the calibrating liquid channel due to breakdown, failure, malfunction, and artificial wrong operation of the biological component-measuring device, and also prevent unnecessary leakage of a body fluid from the examined living organism. Therefore the check valve ensures the prevention of possible damage to the safety of human bodies.

The body fluid-diluting liquid channel should also be provided with a check valve. The check valve placed in the body fluid-diluting liquid channel may prevent a sample taken by the body fluid sampler from flowing into the calibrating liquid channel due to breakdown, failure, malfunction, and artificial wrong operation of the biological component-measuring device, and also prevent unnecessary leakage of a body fluid from the examined living organism. Therefore the check valve ensures the prevention of possible damage to the safety of human bodies.

The present invention employs a first diluent channel that is connected to the sample channel at a location downstream of the first flow path changeover valve. By allowing a diluent, such as a phosphoric acid buffer or a physiological saline, to flow through the first diluent channel, the concentration of a component to be measured can be adjusted to a concentration within such a range that the sensor is able to measure it properly, and the sensitivity and accuracy of the measurement can be enhanced through an improvement in the stability thereof. The phosphoric acid buffer, when the biological component sensor is, for example, a glucose sensor, ensures accurate measurement by the sensor through an adjustment of the pH value of a body fluid taken by the body fluid sampler. Also, when the flow rate of the diluent is increased and/or the diluent includes a surfactant, the time period from the sampling of a body fluid by the body fluid sampler to the measurement by the biological component sensor, or the time constant, can be decreased. A diluent including a surfactant not only improves the flow properties of a fluid, but also expedites mixing of a body fluid and a diluent.

The present invention employs a gas channel connected with the first diluent channel or the junction of the first diluent channel and the sample channel, which makes it possible to send an inert gas such as air or nitrogen gas to the junction of the first diluent channel and the sample channel. The introduction of an inert gas enhances the efficiency of mixing a sample and a diluent, thereby reducing the time period for which a sample flows through the sample channel. The employment of the gas channel enables the device to measure sampled biological components quickly.

The biological component-measuring device according to the present invention has a biological component-measuring device proper and a channel-carrying substrate. The substrate is designed so as to be detachably attachable to the biological component-measuring device proper. The channel-carrying substrate may be used as a disposable member. The substrate is provided with at least the sample channel and the calibrating liquid channel. One end of the sample channel, which is fixed to the substrate, is made so that the end can be detachably attached to a body fluid sampler that is a separate member, not fixed to the substrate. The other end of the sample channel is designed so that it can be detachably attached to a sensor that is also a member not included in or fixed to the substrate. The first flow path changeover valve, which is placed in the middle of the sample channel, is fixed to the substrate. The substrate is fixedly equipped with the calibrating liquid channel as well. One end of the calibrating liquid channel, or the opposite of the other end that is connected to the first flow path changeover valve, is detachably connected to a calibrating liquid supplier, such as a calibrating liquid tank, which is outside the substrate and not included in it. Various structures may be employed for the structure to detachably join the one end of the sample channel to the body fluid sampler, the structure to detachably join the other end of the sample channel to the sensor, and the structure to detachably join the one end of the calibrating liquid channel to the calibrating liquid tank, as long as they are able to achieve liquid-tight connection and the connecting operation can be done easily.

A liquid sample in the sample channel, which is fixed to the channel-carrying substrate, is transferred toward the sensor by a pump. This pump may be fixed to the substrate if it is small and has a simple structure. The pump may also be made up of a part of the sample channel and a roller with which the biological component-measuring device proper is equipped, the roller capable of squeezing the part of the sample channel. As the pump for this biological component-measuring device may be employed a pump capable of transferring a liquid in a channel in one direction by the cooperation of the part of the channel and the roller.

The substrate may be fixedly equipped with a body fluid-diluting liquid channel, a second body fluid-diluting liquid channel, a flushing liquid channel, a first diluent channel, and a gas channel, depending on the purposes, in addition to the sample channel and the calibrating liquid channel.

The body fluid-diluting liquid channel serves as a channel through which a body fluid-diluting liquid used for diluting a body fluid taken from the examined living organism by a body fluid sampler flows. One end of the body fluid-diluting liquid channel is made so that it can be detachably connected to a body fluid-diluting liquid tank, which is a member separate from the substrate and sometimes a part of the biological component-measuring device proper. The other end of the body fluid-diluting liquid channel is made so that it can be detachably joined to the body fluid sampler. For the structures of the respective ends for the detachable connection may be employed those for the ends of the sample and calibrating liquid channels.

The reasons for supplying the body fluid-diluting liquid to the body fluid sampler have been explained hereinabove.

It is preferable that the sample channel and the calibrating liquid channel, and further the body liquid-diluting channel, the second body fluid-diluting liquid channel, the flushing liquid channel, the first diluent channel, and the gas channel, depending on the purposes or at need, should be neatly arranged on and fixed to the substrate, which will be attached to the biological component-measuring device proper. It can make wrong operations avoidable when the ends of the respective channels are connected to members that are not fixed to the substrate, such as the body fluid sampler, the body fluid-diluting liquid tank, the calibrating liquid tank, and the sensor. It also enables the operator to exchange channels easily, and enhances operability and hygiene of the biological component-measuring device.

The calibrating liquid tank should be disposed at a lower level than the body fluid sampler, when the biological component-measuring device according to the present invention is made up of the channel-carrying substrate and the biological component-measuring device proper to which the substrate is attached, and when the device is made up differently. The disposition of the calibrating liquid tank at a lower level prevents a calibrating liquid from flowing backward in the sample channel for some reasons and reaching the body fluid sampler, when the calibrating liquid is supplied from the calibrating liquid tank to the sample channel via the first flow path changeover valve. In summary, arranging the calibrating liquid tank and the body fluid sampler so that the former is placed at a lower location than the latter leads to the prevention of accidents such as an inflow of the calibrating liquid into the examined living organism caused by breakdown or malfunction of the biological component-measuring device.

The calibration method according to the present invention is capable of correcting variation with time in the sample channel and the pump, and further variation with time in the flow rate of the diluent, as well as variation with time in measured values caused by variation with time in the sensor, by one calibrating operation. As a result, the operation necessary for calibrating the entire device is simple, which reduces a time period taken to calibrate it. It is very convenient for the operator. Also, generally, only limited materials that have proven their safety and appropriateness may be used for channels through which liquids such as body fluids flow, in medical devices such as biological components-measuring devices. A simultaneous demand on the materials is a low price. Because variation with time in the channels can be corrected, the present invention makes it possible to choose inexpensive safe materials for the channels among a wide variety of materials that have not been used. Furthermore, the reduction of the time period taken to calibrate a biological component-measuring device also decreases a time period for which a continuous measurement is interrupted. The biological component-measuring device according to the present invention is capable of measuring biological components almost continuously, and is preferably used for measuring the blood sugar level during surgeries.

The calibration method of the present invention makes it possible to carry out a zero point calibration of the biological component-measuring device by supplying a diluent to the sample channel from the first diluent channel prior to sampling a biological component. Generally, the zero point varies very slightly during a measurement of a biological component. Therefore if a zero point calibration is done once prior to the measurement, it will not be necessary in many cases to carry out another zero point calibration until the measurement is completed. When zero point calibrations are not carried out during the measurement, a channel normally connected to the sample channel at a location downstream of the sensor and a flow path changeover valve for the switching to this channel may be omitted. Also, a flushing liquid may be introduced into the sample channel during a measurement of a biological component, which is followed by the introduction of a calibrating liquid into the sensor through a switching of the first flow path changeover valve that makes a selection between the calibrating liquid channel and the sample channel before the flushing liquid reaches the sensor, whereby the biological component-measuring device can be calibrated. This method reduces the total time period taken to carry out calibration.

Furthermore, the flushing liquid may include a component to be measured, for example glucose, in a predetermined amount. The use of a flushing liquid including a predetermined amount of a component being measured makes it possible to calibrate the sensor only. The operator is able to judge whether the sample channel should be changed to a new one based on the result of the calibration of the sensor only. In other words, maintenance of the biological component-measuring device can be done exactly.

The calibration method of the present invention includes the operational step of introducing a flushing liquid into the sample channel at a flow rate larger than the flow rate of the sample, which is called "the first step", during a measurement of a biological component. The introduced flushing liquid cleans elements such as the sample channel, the body fluid sampler and the sensor, and discharges undesired matters such as clots and gelled body fluid as well as the sample from the biological component-measuring device. When the flushing liquid does not include the component being measured, a zero point calibration can be carried out even under the condition where the body fluid sampler is connected to the human body. The method also includes the operational step of introducing a calibrating liquid into the sensor by switching the first flow path changeover valve placed in the sample channel so that the passing of the calibrating liquid is selected, after the first portion of the flushing liquid is introduced into the sample channel and the sensor, which is called "the second step". The use of a calibrating liquid including a particular component being measured enables the sensor to measure the component in known concentrations and to output corresponding measured values. The operator is able to calibrate the biological component-measuring device as a whole, preparing a working curve based on these measured values and the value obtained in the first step. The method further includes the operational step of introducing a second portion of the flushing liquid at a flow rate smaller than the first flow rate into the sample channel at a location upstream of the first flow path changeover valve and into the body fluid sampler during the second step, which is called "the third step". The third step serves to prevent the body fluid such as blood from clotting in the sample channel between the body fluid sampler and the first flow path changeover valve during the calibrating operations.

DETAILED DESCRIPTION OF THE PREFERRED EMBODIMENTS

1. The Reference Numerals

Figure 1:
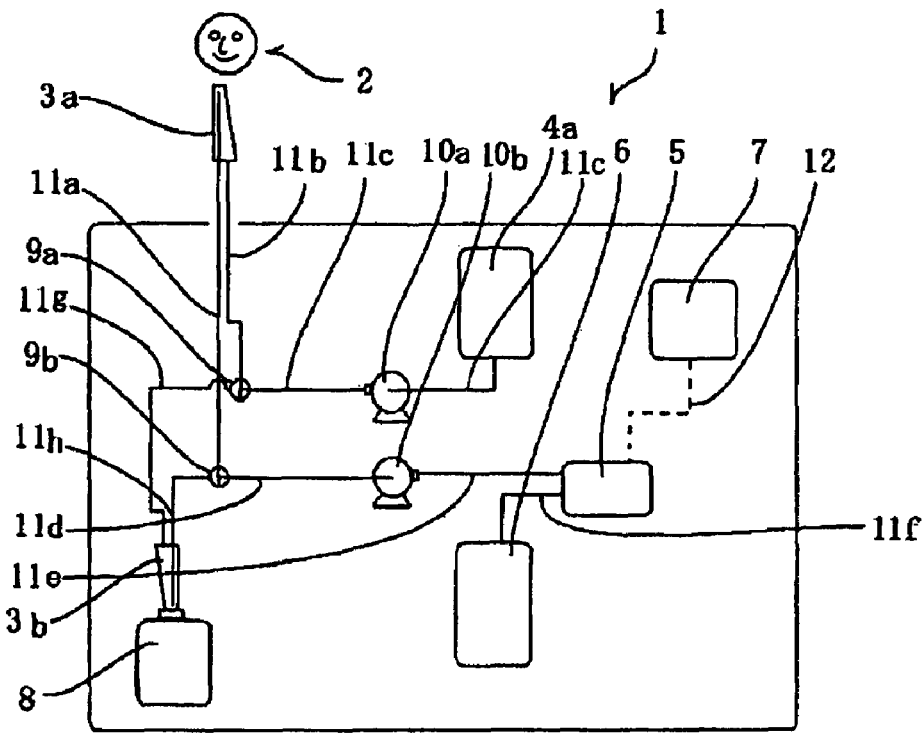
FIG. 1 is a schematic block diagram showing an embodiment of the biological component-measuring device equipped with a body fluid-diluting liquid channel according to the present invention.

1 . . . biological component-measuring device; 2 . . . examinee; 3a . . . body fluid sampler; 3b . . . calibrating liquid sucker; 4a . . . body fluid-diluting liquid tank; 4b . . . diluent tank; 5 . . . sensor; 6 . . . waste liquid tank; 7 . . . sensor signal processor; 8 . . . calibrating liquid tank; 9a . . . second flow path changeover valve; 9b . . . first flow path changeover valve; 9c, 9d, 9e . . . third, fourth and fifth flow path changeover valves; 10 . . . pump tube; 10a, 10b, 10c, 10d, 10e, 10f . . . pump; 11a . . . first portion of a sample channel; 11b . . . second portion of a body fluid-diluting liquid channel; 11c . . . third portion of the body fluid-diluting liquid channel; 11d . . . second portion of the sample channel, 11e . . . third portion of the sample channel; 11f . . . waste liquid channel; 11g . . . second body fluid-diluting liquid channel; 11h . . . calibrating liquid channel; 11i . . . first portion of a first diluent channel; 11j . . . second portion of the first diluent channel; 11q . . . second diluent channel; 11k . . . first portion of a flushing liquid channel; 11m . . . second portion of the flushing liquid channel; 11r . . . third portion of the flushing liquid channel; 11n . . . gas channel; 11o . . . fourth portion of the sample channel; 11p . . . gas-discharging channel; 12 . . . sensor signal transmission line; 13 . . . flushing liquid tank; 14, 14a, 14b, 14c, 14d . . . check valve; 15 . . . mixer; 15a . . . mixer proper; 15b . . . inner fluid flow space, 15c . . . rugged part; 16 . . . gas-liquid separator; 17 . . . channel-joining member; 18 . . . heater; 19 . . . channel-carrying substrate; 20a . . . roller; 20b . . . rotator; 20c . . . stick; 20d . . . holding plate; 21 . . . pump; 21a . . . pressing member; 21b . . . eccentric rotating cam; 21c . . . rotating shaft; 21d, 21e . . . holding plate; 21f . . . hole; 21g . . . first poppet valve; 21h . . . second poppet valve; 21i . . . tube molded in the shape of a pillow; 22 . . . pillow-type reciprocating pump

2. The Detailed Description

The present invention relates to improving a biological component-measuring device that measures various biological components included in the body fluids of a living organism, a typical example of which is a human. The body fluids in a living body include, for example, blood, urine, lymph or cerebrospinal fluid, or mixtures thereof. The biological components, the qualitative or quantitative analysis of which is necessary for medical practice, may include glucose, urea, uric acid, lactose, sucrose, lactate, ethanol, glutamic acid, ammonia, creatinine, and oxygen. Medical practice may sometimes require measurement of other properties, such as the pH value and the oxygen concentration, of body fluids. In the context of the present invention, the term "biological components" includes properties such as the pH value and the oxygen concentration.

A biological component-measuring device is a device necessary for medical doctors and veterinarians to understand the condition of a living organism accurately. Examples of medical support devices include artificial endocrine pancreas devices for measuring a blood sugar level in blood and based on the measurement results supplying insulin to a living organism, dialyzers for dialyzing, urea concentration meters for measuring the urea content included in the body fluids of a living organism, uric acid concentration meters for measuring a uric-acid content in the body fluids of a living organism, sugar concentration meters for measuring lactose and sucrose in the body fluids of a living organism, lactic acid concentration meters for measuring lactic acids such as lactate, glutamic acid concentration meters for measuring the glutamic acid content in the body fluids of a living organism, ammonia concentration meters for measuring an ammonia content in the body fluids of a living organism, and creatinine concentration meters for measuring a creatinine content in the body fluids of a living organism.

These various biological component-measuring devices are necessary to take exact medical action. Thanks to the present invention, the clinical examiner is able to make a biological component-measuring device ready for operation efficiently and hygienically. For the sensor included in the biological component-measuring device to measure a biological component may be employed various sensors depending on the kinds of biological components to be measured. Examples of such sensors may include biosensors, such as enzyme sensors utilizing enzymes, microorganism sensors employing microorganisms, and hybrid sensors utilizing enzymes and microorganisms. The enzyme or microorganism utilized in such a biosensor is selected depending on the target to be measured, or the biological component. For example, when the target to be measured is glucose, β-D-glucose oxidase or *Pseudomonas fluorecens* may be employed as biosensor. When the target is urea, urease may be employed as biosensor; when the target is uric acid, uricase may be employed; for lactate may be used lactate oxidase; for lactose may be employed lactase or β-galactosidase; for ethanol may be employed alcohol oxidase or *Trichosporon brassicaes*; for glutamic acid may be employed glutamate dehydrogenase or *Escherichia coli*; and for ammonia may be employed nitrifying bacteria.

For the sensor may be employed, for example, a biosensor made by coating a carbon electrode with an osmium polymer, drying the coated electrode at room temperature, applying an enzyme solution thereto to make a film, and immobilizing the enzyme by a cross-linking agent such as glutaraldehyde, when glucose is measured. This biosensor causes an oxidation reaction between peroxide and a peroxidase enzyme, which is immobilized in the osmium polymer, and the reaction is followed by a reduction reaction between the osmium polymer, the peroxidase and the electrode. The electrode potential during these reactions is 0 mV compared with the electrode potential of the silver-silver chloride electrode. Therefore the utilization of the glucose oxidase for the enzyme for the oxidation reaction leads to a quick detection of glucose and an easy measurement of the concentration thereof. The glucose sensor may include, other than that explained above, a glucose sensor including an osmium (II)-bipyridine complex, one including a ruthenium complex, and a glucose sensor with an electrode modified with a polypyrrole into which a tris-osmium complex is immobilized. Among these various glucose sensors, the biosensor employing the osmium polymer is preferable. Suitable glucose sensors are film sensors having a work electrode of platinum, silver or carbon, and an enzyme film of an osmium polymer impregnated with peroxidase.

The biological component-measuring device according to the present invention is capable of dealing with one or more measurable biological components. When two or more biological components are measured, the device should be equipped with two or more biosensors in the biological component-measuring channel. Another way to measure several components may be to make the biological component-measuring channel branch off and to provide each branch channel with one or more biosensors. The body fluids sampled from a living organism may be sampled body fluids as they are, such as blood, urine, lymph and cerebrospinal fluid, or mixtures of such body fluids and other liquids such as physiological saline, diluents or buffers.

The constitution of the biological component-measuring device according to the present invention can be explained by referring to the schematic block diagram shown in FIG. 1. A biological component-measuring device 1 according to the present invention in its basic constitution includes a body fluid sampler 3a; a sensor 5; first, second and third portions 11a, 11d, 11e of a sample channel through which a body fluid is transferred from the body fluid sampler 3a to the sensor 5; a pump 10b placed in fourth and fifth portions of the sample channel to forcibly transfer a sample including the body fluid that flows in the sample channel; a calibrating liquid tank 8 in which a calibrating liquid is stored; a calibrating liquid channel 11h to guide the calibrating liquid to the second portion 11d of the sample channel; and a first flow path changeover valve 9b serving to connect the first portion 11a of the sample channel and the calibrating liquid channel 11h with the second portion 11d of the sample channel, and to switch the connection with the second portion 11d of the sample channel between the first portion 11a of the sample channel and the calibrating liquid channel 11h so that either of the taken sample and the calibrating liquid will flow into the second portion 11d of the sample channel. Although the calibrating liquid tank 8 includes the word "tank", the "tank" means a container in which liquid is stored, such as a bag, a can or a box. Tanks including a body fluid-diluting liquid tank, a diluent tank, and a flushing liquid tank, which will be explained hereinafter, are also used in the present specification to denote general containers.

Although the sensor per se may have functions of processing measured values, storing them, outputting and displaying them, the device should preferably have a sensor signal transmission line 12 and a sensor signal processor 7 to send signals outputted by the sensor through the sensor signal transmission line 12 to the sensor signal processor 7 in which measured values are processed and stored and which outputs and displays the measured results or sends them to other units. When the biological component-measuring device is actually operated, a waste liquid, or a sample including a body fluid after measurement by the sensor, should preferably be guided to a waste liquid tank 6 through a waste liquid channel 11f, and then disposed of hygienically. Normally, a body fluid-diluting liquid, such as an anticoagulant, should be introduced into the body fluid sampler 3a in order to prevent a sampled body fluid from changing in its properties, and a sampled body fluid should be diluted with the body fluid-diluting liquid at the same time as the body fluid is taken. The diluted body fluid will be used as a sample to be measured. As shown in FIG. 1, the device should further include a body fluid-diluting liquid tank 4a in which a body fluid-diluting liquid is stored, and a first portion 11c of a body fluid-diluting channel 11c, a second portion 11b of the body fluid-diluting channel, and a pump 10a, through which the body fluid-diluting liquid is introduced into the body fluid sampler 3a. The employment of this structure should be accompanied by the placement of a second flow path changeover valve 9a in the first portion 11c of the body fluid-diluting liquid channel at a location downstream of the pump 10a with which a second body fluid-diluting liquid channel 11g is connected, so that the body fluid-diluting liquid can be introduced to a calibrating liquid sucker 3b that is provided to draw a body fluid-diluting liquid from the calibrating liquid tank 8 and send it to the calibrating liquid channel 11h. The calibrating liquid sucker 3b has a structure similar to the structure of the body fluid sampler 3a. The former should have such a structure that the ratio of the amount of a body fluid to that of the body fluid-diluting liquid in the body fluid sampler 3a is the same as the ratio of the amount of the calibrating liquid to that of the body fluid-diluting liquid in the calibrating liquid sucker 3b. Normally, a same one as the body fluid sampler 3a should be used for the calibrating liquid sucker 3b, which makes the latter ratio the same as the former ratio.

The measurement of a biological component by the biological component-measuring device 1, and the method of calibration will now be described. Firstly, a biological component-measuring device 1 in a capable condition is prepared. In this state, the first flow path changeover valve 9b makes the first portion 11a of the sample channel communicate with the second portion 11d of the sample channel, and blocks the calibrating liquid channel 11h. This operation can be done easily when a cross valve is used for the first flow path changeover valve 9b. On the other hand, the second flow path changeover valve 9a makes the second portion 11b of the body fluid-diluting liquid channel communicate with the first portion 11c of the body fluid-diluting liquid channel, and blocks the second body fluid-diluting liquid channel 11g. Then, the pumps 10a, 10b are activated, and while a body fluid-diluting liquid is being supplied to the body fluid sampler 3a, the body fluid sampler 3a transfers a sample including a taken body fluid to the sensor 5. In this state, the respective discharges of the pump 10a and the pump 10b are adjusted so that the amount of the supplied body fluid-diluting liquid is larger than that of the sample drawn to the first portion 11a of the sample channel from the body fluid sampler 3a. If the amount of the sample drawn to the first portion 11a of the sample channel is not larger than that of the body fluid-diluting liquid supplied to the body fluid sampler, the body fluid cannot be taken through the body fluid sampler 3a. The body fluid-diluting liquid may be anything as long as it does not affect living organisms adversely, interfere with measurement by the sensor, change a body fluid in its properties, or coagulate a body fluid. Preferable is a physiological saline or Ringer's solution. If the amount used is small, other liquids such as distilled water or a phosphoric acid buffer may be used. In order to prevent a body fluid such as blood from gelling at the tip of a catheter, Ringer's solution, the physiological saline, the distilled water into which an anticoagulant is incorporated may be used preferably. Examples of the anticoagulant may include heparin, Nafamostat mesylate and urokinase.

Thus, a biological component in the taken body fluid can be measured. If the measurement is continued, the biological component can be measured continuously. In this specification, the taken body fluid or a solution made by diluting the taken body fluid with a body fluid-diluting liquid may sometimes be called "sample". When the biological component-measuring device is, for example, a blood sugar level-measuring device, a continuous measurement over one to several days can be possible. However, sensors for measuring biological components, including blood sugar level-measuring sensors, are often biosensors utilizing enzymes or microorganisms as stated above. Such sensors usually require calibration at intervals from several hours to several tens of hours. If calibration with such frequencies is neglected, accurate measured values often cannot be obtained. Also, channels, such as the sample channel and the body fluid-diluting channel, and pumps for transferring liquids are often so-called disposable ones from the viewpoint of hygiene, which makes the manufactures select cheap tubes such as vinyl chloride tubes or polyethylene tubes for these elements. The elements, such as channels and pumps, made of these cheap tubes are apt to cause variation in the flow rate of the sample and the diluting ratios due to variation with time in the thickness of the channels, especially in the inner diameter thereof, or the transverse sectional area thereof; variation in the operating temperature while they are being used; and variation in the properties of the pumps. Such variations in the flow rate and the diluting ratios cannot be taken care of by calibration of the sensors only. Therefore, the present invention employs the method of calibrating all of the sample channel, the body fluid-diluting liquid channel, the pumps 10b, 10a, and the sensor 5 as a whole by introducing the calibrating liquid from the first portion 11a of the sample channel, which provides accurate calibration to the entire biological component-measuring device 1. The employment of this method makes it possible to use channels made by such materials that change in the thickness of the channels, especially the inner diameter thereof, or the transverse sectional area thereof when the channels are used for a long time. Generally, only limited materials that have proven their safety and appropriateness may be used for channels through which liquids such as body fluids flow, used in medical devices such as biological components-measuring devices. A simultaneous demand on the materials is a low price. Because variation with time in the channels can be corrected, this embodiment makes it possible to choose inexpensive safe materials for the channels among a wide variety of materials that have not been used. Therefore the first flow path changeover valve 9b that switches between the first portion 11a of the sample channel and the calibrating liquid channel 11h should be placed near the outlet of the body fluid sampler 3a. Furthermore, when a body fluid-diluting liquid is introduced into the body fluid sampler 3a, the body fluid-diluting liquid in the same amount as the body fluid-diluting liquid that was used during the sampling of the body fluid should be introduced into the calibrating liquid sucker 3b by the switching of the second flow path changeover valve 9a. This operation makes the ratio of the amount of the body fluid-diluting liquid to that of the calibrating liquid the same as the ratio of the amount of the body fluid-diluting liquid to that of the body fluid, which simplifies the calibration and is advantageous.

The biological component-measuring device 1 according to the present invention should be used in the state where the body fluid sampler 3a is placed at a higher level than the other parts and members such as the body fluid-diluting liquid tank 4a, the calibrating liquid tank 8, the sensor 5, and the waste liquid tank 6.

The communication between the body fluid sampler 3a and the calibrating liquid tank 8 is not blocked by elements such as a tube pump. Therefore, if an actual operation of body fluid sampling is performed by a biological component-measuring device where the calibrating liquid tank is located at a higher level than the examined living organism, there is a probability that the calibrating liquid may flow into the living organism by gravitation, while the flowpath changeover valve is switching the channels or when malfunction occurs in the valve or other elements. There is a weak probability that the calibrating liquid may endanger the examinee, or the living organism, because the calibrating liquid is a solution including the same component of the living organism; the calibrating liquid is a glucose solution in almost the same concentration as the glucose concentration in the living organism, when the glucose concentration is measured. However, the calibrating liquid does not require sterilization by nature. If the calibrating liquid flows into the living organism, infectious diseases might be caused by it. The calibrating tank 8 should preferably be placed at a lower level than the body fluid sampler 3a, which will leads to the prevention of such infection. In actual operations, the calibrating liquid tank 8 should preferably be placed below, for example abed on which the living organism from which a body fluid is taken, such as a human. Because the height of the bed is typically about 45 cm, this arrangement will be realized if the liquid level in the calibrating liquid tank 8 is set to 45 cm or less from the floor.

In summary, the body fluid sampler 3a should be attached to a living organism at a higher level than the biological component-measuring device 1, especially the calibrating liquid tank 8, and then sampling of the body fluid and calibration of the biological component-measuring device 1 should be carried out. There is a probability that the calibrating liquid may adversely affect the living organism if the calibrating liquid flows backward into the living organism, as stated above. Therefore in a state where a body fluid in the living organism and a liquid in the body fluid sampler 3a may be exchanged, the calibrating liquid tank 8 should be disposed at a lower level than the body fluid sampler 3a when the latter is attached to the living organism. This arrangement will check an inflow of the calibrating liquid into the living organism by gravitation, even if the first portion 11a of the sample channel, the first flow path changeover valve 9b or the calibrating liquid channel 11h works wrongly, or the operator makes some errors. However, the body fluid sampler 3a does not always have to be disposed at a higher level than the liquid level in the calibrating liquid tank 8; there is no probability that the calibrating liquid flows into the living organism, when the summation of the pressure head and the potential head of a body fluid, such as blood, at the position where the body fluid sampler 3a is connected to the living organism is larger than the potential head of the liquid level in the calibrating liquid tank 8. Therefore when the body fluid sampler 3a is connected to, for example a peripheral vein in which the blood pressure is about 18 mmHg, the liquid level in the calibrating liquid tank 8 may be about 240 mm higher than the position at which the body fluid sampler 3a is connected to the living organism. When the body fluid sampler 3a is connected to an artery, in which the blood pressure is higher than in a vein, the calibrating tank 8 may be disposed at a further higher level.

The waste liquid tank should be disposed so that a waste liquid naturally drips from the waste liquid channel to the surface of the liquid in the tank, with the waste liquid channel not being in the liquid. These elements should be arranged so that a waste liquid does not flow back through the sample channel due to the principle of the siphon. The pump placed in each channel preferably has a function of preventing backflow. Examples of such a pump may include tube pumps and linear peristaltic pumps. These arrangement and selection make it possible to prevent a backflow of the liquid in each channel into the living organism caused by abnormal movements of the liquid and to check an unexpected inflow of the liquid into the tanks, such as the calibrating liquid tank, with which the biological component-measuring device is provided.

Figure 2:
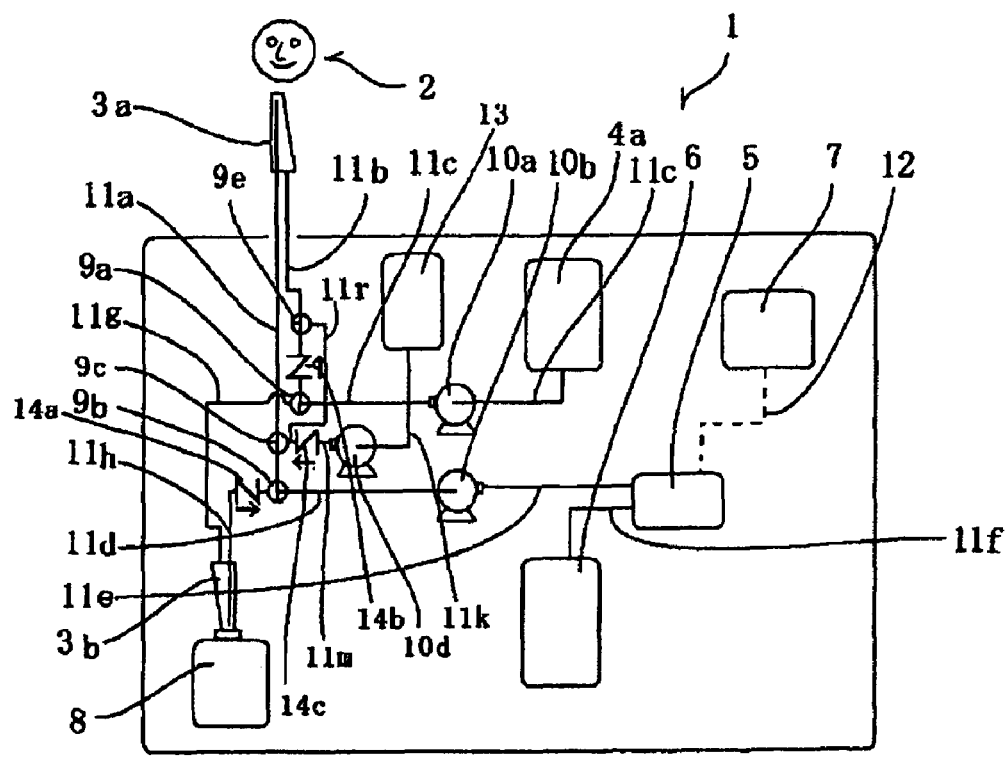
FIG. 2 is a schematic block diagram showing an embodiment of the biological component-measuring device further equipped with a flushing liquid channel according to the present invention.

The example of the biological component-measuring device according to the present invention shown in FIG. 2 has a flushing liquid channel 11m in addition to the device that I have explained, referring to the example shown in FIG. 1. The flushing liquid channel 11m, or the second portion 11m of the flushing liquid channel, can communicate with the first portion 11a of the sample channel via a third flow path changeover valve 9c, and with the second portion 11b of the body fluid-diluting liquid channel via a fourth flow path changeover valve 9e. Furthermore, the calibrating liquid channel 11h, the second portion 11b of the body fluid-diluting liquid channel, and the second portion 11m of flushing liquid channel are respectively provided with check valves 14a, 14b and 14c. When the body fluid sampler 3a is kept attached to the living organism during the calibration of the biological component-measuring device shown in FIG. 1, a sample including the body fluid remains in the body fluid sampler 3a and the first portion of the sample channel 11a. When the sample remains in the device in such a state, there is a probability that the body fluid included in the sample, such as blood, may coagulate. Especially when the body fluid-diluting liquid is not used, or the amount of the body fluid-diluting liquid used for the dilution is small, the component in the sample is prone to coagulate. The embodiment of the present invention shown in FIG. 2 is provided with equipment to introduce the flushing liquid in order to wash the respective insides of the body fluid sampler 3a and the first portion 11a of the sample channel when or just before the calibrating operation is begun, so that the measurement can be resumed immediately after the completion of the calibration and the body fluid included in the sample is prevented from coagulation or deterioration. The equipment to introduce the flushing liquid into the device includes a flashing liquid tank 13, a pump 10d for sending the flushing liquid, the first portion 11k, 11m of the flushing liquid channel, the third and fourth flow path changeover valves 9c, 9e, and preferably the check valve 14c. If a pump with a function of preventing backflow, such as a tube pump or a linear peristaltic pump, is used for the pump 10d for sending the flushing liquid, a backflow from the sample channel or the body liquid-diluting liquid to the flushing liquid channel should not occur principally and the third and fourth flow path changeover valves 9c, 9e and the check valve 14c may be omitted. However, if there is something wrong with the flushing liquid channel or the pump 10d for sending the flushing liquid, the third and fourth flow path changeover valves 9c, 9e that have the function of cross valves and the check valve 14c effectively prevent backflow.

When the flushing is commenced, the pump 10d is activated and the third flow path changeover valve 9c and/or the fourth flow path changeover valve 9e is switched so that a flushing liquid stored in the flushing liquid tank 13 is sent to the first portion 11k of the flushing liquid channel, guided to the second portion 11m of the flushing liquid channel by the pump 13, and further introduced through the check valve 14c to the first portion 11a of the sample channel and/or the second portion of 11b the body fluid-diluting channel via the third flow path changeover valve 9c and/or the fourth flow path changeover valve 9e. A part of the flushing liquid reaches the sensor through the sample channel and is discharged to the waste liquid tank through the waste liquid channel. Another part of the flushing liquid flows into the living organism through the body fluid sampler. Thus, the channels and elements such as the sample channel, the sensor and the body fluid sampler are washed with the flushing liquid, so that clots and gelled body fluid as well as the sample are discharged from the biological component-measuring device. This operation is called the "removal of clots". The first portion of the sample channel 11a, the sensor, and the body fluid sampler 3a are filled with the flushing liquid, which removes a probability that the biological component may coagulate in them. Then, the first flow path changeover valve 9b and the second flow path changeover valve 9a are switched so that the calibrating liquid is introduced from the calibrating liquid channel 11h into the second portion 11d of the sample channel and the portion downstream thereof, which is followed by the calibration of the biological component-measuring device 1. The third flow path changeover valve 9c preferably blocks the communication between the first portion 11a of the sample channel and the second portion 11m of the flushing liquid channel, and the fourth flow path changeover valve 9e between the second portion 11b of the body fluid-diluting liquid channel and the second portion 11m of the flushing liquid channel, during a normal measurement of a biological component.

The sensor may also be washed with the calibrating liquid other than the flushing liquid. After the completion of the washing with the flushing liquid, the first flow path changeover valve 9b and the second flow path changeover valve 9a are respectively switched so that the second portion of the sample channel and the first portion of the body fluid-diluting liquid channel respectively communicate with the calibrating liquid tank 8, which keeps the first portion 11a of the sample channel filled with the flushing liquid. Even if the pump 10d for sending the flushing liquid is stopped in this state, coagulation can be prevented because it is the same as the state where the so-called "physiological saline lock" is attached to the living organism. When the pump 10d for sending the flushing liquid is not stopped but driven so as to send the liquid little by little, for example, at a very small flow rate, the possibility of coagulation can be further reduced.

The flow rate of the flushing liquid during the calibration should be smaller than that of the flushing liquid during the "removal of clots" operation. The introducing operation of the flushing liquid in this state is called the "prevention of clotting" operation. The flushing liquid is introduced at a flow rate from 5 to 500 mL/hour, preferably from 100 to 300 mL/hour for about 1 to 60 seconds, preferably for about 3 to 20 seconds during the removal of clots operation, while it is introduced at a flow rate from 0.5 to 60 mL/hour, preferably from 1 to 20 mL/hour during the prevention of clotting operation, with, for example, a biological component-measuring device for a typical artificial endocrine pancreas device. When a biological component-measuring device has very small dimensions, an even smaller amount of the flushing liquid may be used as long as clots in the channel can be removed and coagulation can be prevented. When there is little or no possibility that body fluid components can coagulate even if the sample remains in the section of the first portion 11a of the sample channel between the third flow path changeover valve 9c and the first flow path changeover valve 9b, the calibration may be commenced at the same time as the introduction of the flushing liquid into the first portion 11a of the sample channel and the body fluid sampler 3a. For the flushing liquid may be used a liquid that are not harmful to living organisms when it flows into them, such as a physiological saline. If it is desired that the inflow of the flushing liquid into the living organism be avoided as much as possible, the introduction of the flushing liquid may be stopped after the first portion 11a of the sample channel and the body fluid sampler 3a are filled with the flushing liquid. The flushing liquid may be anything as long as it does not change the body fluid or the sample in its properties, coagulate it, interfere with measurement by the sensor, or affect living organisms adversely if the flushing liquid flows into them. Preferable is a physiological saline or Ringer's solution. If the amount used is small, distilled water may be used. Ringer's solution, the physiological saline, the distilled water into which an anticoagulant, such as heparin, Futhan or urokinase, is incorporated may be used appropriately. The anticoagulant, however, preferably should not be used, because it affects the antithrombogenicity mechanism of a patient in an unstable condition, for example, under emergency intensive care, and sometimes provides the opposite effect, or causes body fluids including blood to coagulate quickly.

The functions of check valves 14a, 14b and 14c will be described. These check valves prevent a sample taken by the body fluid sampler 3a from penetrating into unexpected parts due to breakdown, failure, malfunction, and artificial wrong operation of the biological component-measuring device. The check valves 14a, 14b prevent the sample from flowing back into the calibrating liquid tank 8, even when the calibrating liquid channel 11h is not provided with the first and second flow path changeover valves 9a, 9b. The check valve 14b also keeps the sample from flowing back into the body fluid-diluting liquid tank 4a. The check valve 14c prevents the sample from flowing back into the flushing liquid tank 13. The advantages of preventing such backflows include not only the preclusion of the liquid in each tank from contamination but also the prevention of a body fluid from unnecessarily leaking from a living organism. Especially when the living organism is a human, the objective of providing these check valves is to ensure the preclusion of a probability that the human's safety may be damaged. If the channels are wrongly assembled, the flow path changeover valves are wrongly operated, there is a failure in the channels and equipment, or the human is placed at a higher location than the biological component-measuring device including the calibrating liquid tank, there is a probability that body fluids, such as blood, may be unexpectedly lost from the human. The check valves are effective in preventing such accidents. There is also a probability that the first flow path changeover valve 9b and the first flow path changeover valve 9a may allow all the relevant channels to communicate, depending on the structures of the valves, when the valves are switched. The check valves 14a, 14b, if provided, will be able to prevent backflows also in these situations. The channels, through which the sample flows, such as the sample channel 11a, 11d, 11e, 11o and the waste liquid channel 11f, may also be provided with check valves, although they are not placed in this embodiment. These check valves are capable of preventing a body fluid from unnecessarily leaking from the living organism as well as precluding a sample from flowing back into the living organism, the calibrating liquid tank 8, the body fluid-diluting liquid tank 4a, the flushing liquid tank 13 or the sensor 5.

Figure 3:
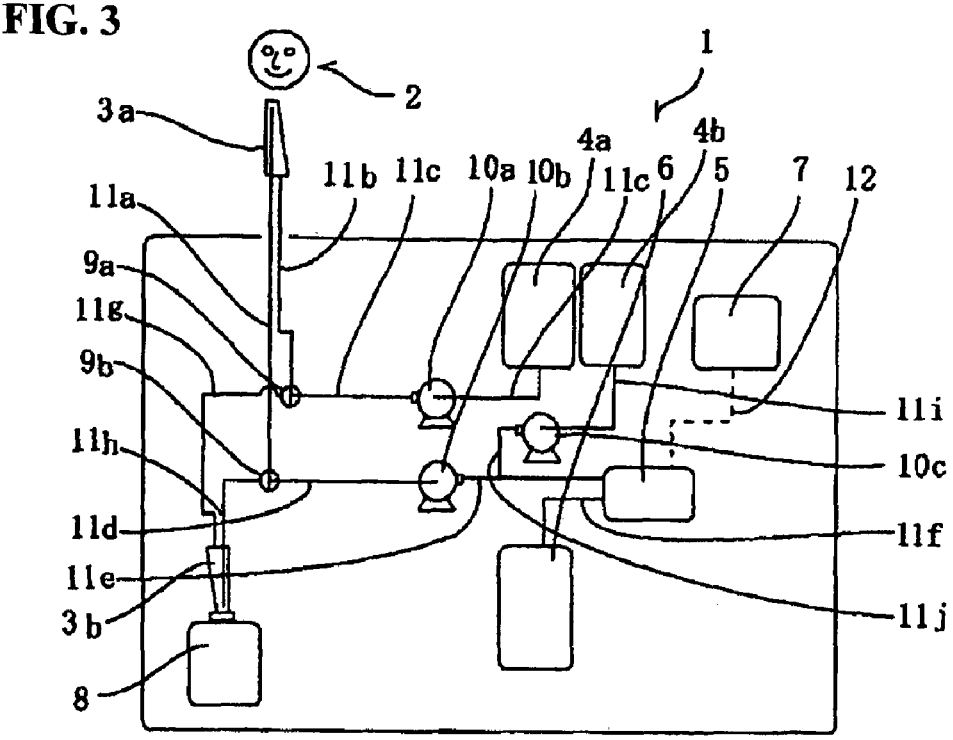
FIG. 3 is a schematic block diagram showing an embodiment of the biological component-measuring device equipped with a body fluid-diluting liquid channel and a first diluent channel according to the present invention.

An embodiment of the biological component-measuring device according to the present invention shown in FIG. 3 introduces a diluent into a third portion 11e of the sample channel, which enlarges the measuring range of the sensor and improves the stability of the measurement, which, in turn, leads to an improvement in the measuring sensitivity and accuracy. Also, an enlargement of the flow rate can shorten the time necessary for the sample to reach the sensor, which can reduce the time lag. This feature greatly contributes to the safety of devices, such as artificial endocrine pancreas devices, where a feedback control is carried out, or a liquid medicine in an amount is injected to the patient based on the results of the measurement, because the feature ensures the stability of the control. This embodiment of the body fluid-measuring device further includes a diluent tank 4b, a first portion 11i of a first diluent channel for introducing a diluent from the diluent tank 4b to a pump 10c, the pump 10c for drawing the diluent out of the diluent tank 4b and forcibly sending it to a third portion 11e of the sample channel, and a second portion 11j of the diluent channel through which the diluent is sent to the third portion 11e of the sample channel from the pump 10c, in addition to the elements of the biological component-measuring device shown in FIG. 1. The diluent should preferably introduced into the third portion 11e of the sample channel, located downstream of the pump 10b for transferring the sample. A feature of this embodiment is to supply a diluent to the third portion 11e of the sample channel so that the sample will be in such a desired concentration that the sensitivity and precision of the sensor are in their best condition. The diluent is capable of stabilizing the pH of the sample, making the temperature of the sample constant, precluding an emission of gas from the sample in the sensor, and preventing the sample from changing in its properties. The diluent may be anything as long as it does not interfere with measurement by the sensor, or change the sample in its properties. Preferable examples may include a physiological saline, a phosphoric acid buffer and the body fluid-diluting liquid as explained hereinbefore. The phosphoric acid buffer has a function of enhancing the ability of transferring electric charges in the diluted sample, and therefore is an appropriate diluent. The diluent may sometimes include a surfactant. The diluent including a surfactant not only enhances the flow properties of the sample, but also expedites mixing of the sample with the diluent. The enhancement in the flow properties of the sample reduces the time period from the sampling of a body fluid by the body fluid sampler to the measurement of the sampled, or the time constant.

The diluent for, for example, the measurement of a blood sugar level by the biological component-measuring device according to the present invention should preferably be a liquid capable of diluting a sample transferred through the third portion 11e of the sample channel, and keeping the pH value of the sample to be sent to the sensor 5 constant. An example of such a liquid is a phosphoric acid buffer. When a buffer is employed for the diluent, a stable measurement of a blood sugar level can by carried out by a highly pH-sensitive sensor because the pH value of the sample can be kept constant. Also, if a relatively large amount of the diluent whose temperature is kept constant is used, the sample diluted with this diluent can be quickly introduced to the sensor at a stable temperature, which improves the accuracy of the measurement.

Figure 4:
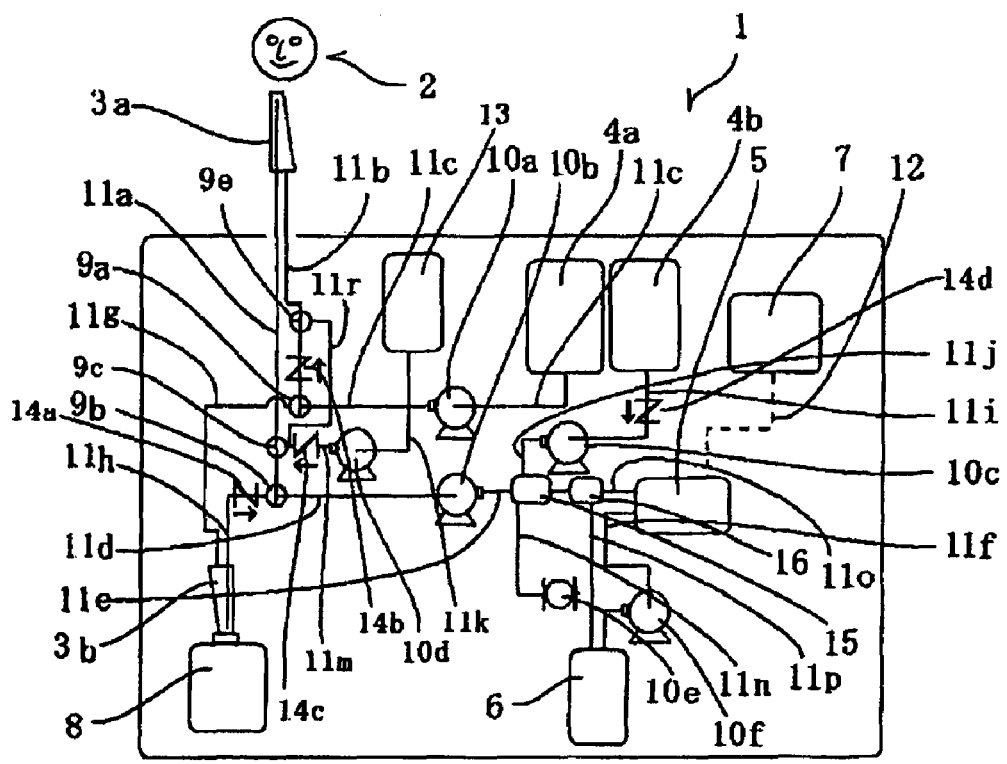
FIG. 4 is a schematic block diagram showing an embodiment of the biological component-measuring device equipped with a flushing liquid channel, a body fluid-diluting liquid channel, a first diluent channel and a gas channel according to the present invention.

An embodiment of the biological component-measuring device according to the present invention shown in FIG. 4 further includes a gas channel through which a gas to expedite mixing, such as air, is introduced to the first diluent channel or the joint of the first diluent channel and the sample channel, in order to make the mixing of the sample with the diluent complete in the third portion 11e of the sample channel to which the diluent has been supplied, in addition to the combination of the embodiment of FIG. 2 and the embodiment of FIG. 3. In the mixing part of the third portion 11e of the sample channel is placed a mixer 15, and at a location downstream of the mixer a gas-liquid separator 16 so that the mixture is effectively stirred by the mixer 15 and by the introduction of air. Gas is separated from the sample that has undergone the stirring and mixing, by the gas-liquid separator 16, and the separated gas is removed and discharged through a gas-discharging channel 11p to a waste gas tank 6. Only the sample that has been mixed uniformly is sent to the sensor. If there is an excessive amount of the sample, an unnecessary portion of the sample is also discharged from the gas-liquid separator 16 through the gas-discharging channel 11p to the waste gas tank 6. When the sample that has been thoroughly and uniformly mixed with the diluent is sent to the sensor 5, the measuring stability of the sensor 5 is enhanced and the measuring sensitivity and the measuring accuracy are further improved. The sample, after the completion of the measurement by the sensor 5, is sucked by a pump 10f whose discharge is set to a value less than the total of the discharge of the pump 10b and that of the pump 10c, and discharged to the waste liquid tank 6. The first diluent channel should preferably be provided with a check valve 14d, in the same way as the body fluid-diluting liquid channel.

Figure 5:
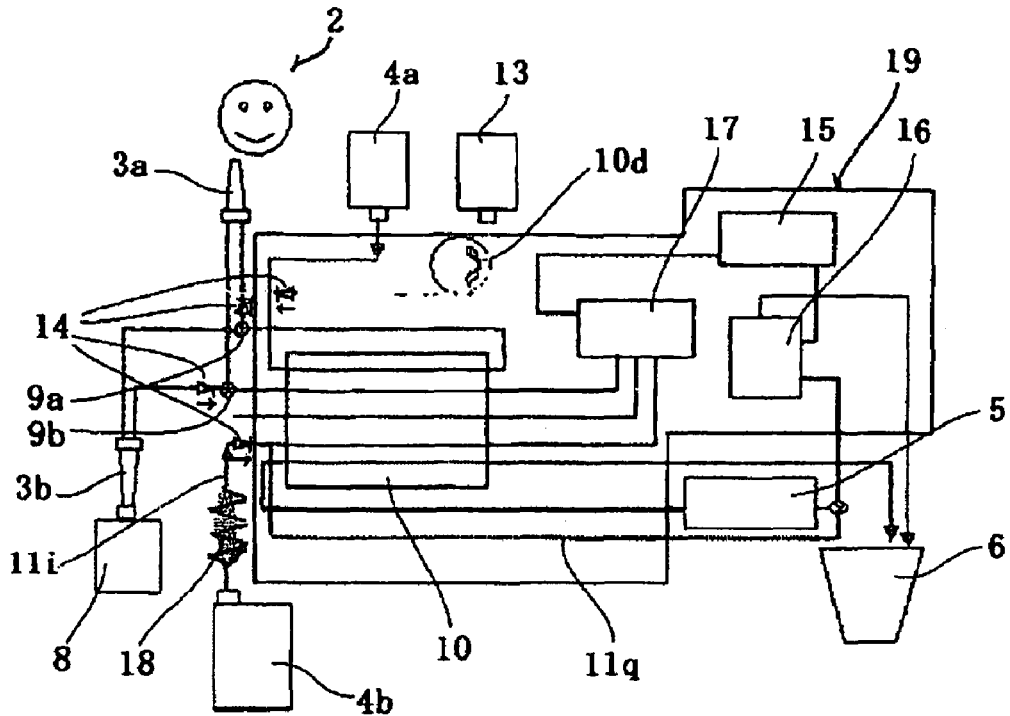
FIG. 5 is a schematic block diagram showing an embodiment of the biological component-measuring device to which a channel-carrying substrate is attached, according to the present invention.
Figure 6:
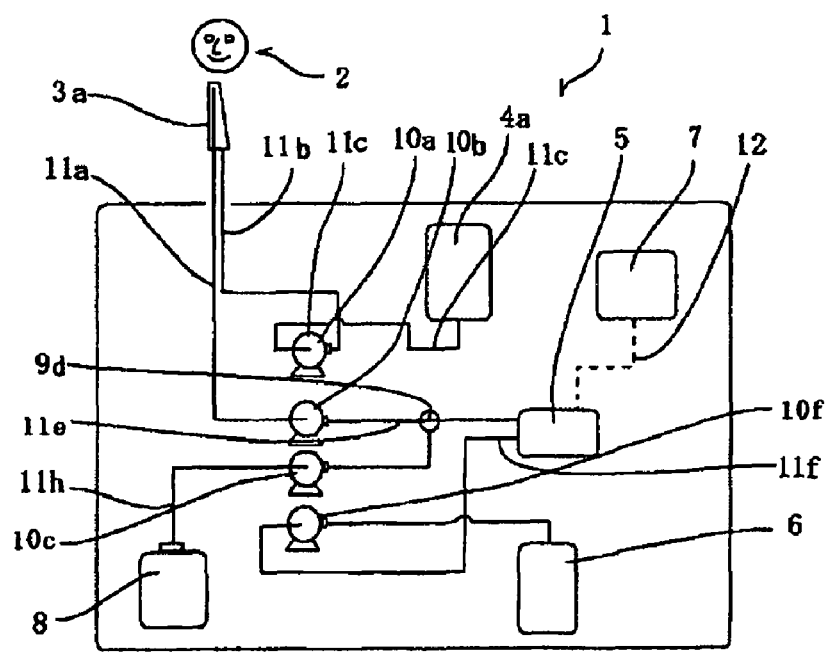
FIG. 6 is a schematic block diagram showing an example of a conventional biological component-measuring device.

FIG. 5 shows an embodiment in which a channel-carrying substrate is disposed in the embodiment of the biological component-measuring device shown in FIG. 4. On the channel-carrying substrate 19 of the embodiment of FIG. 5 are arranged various kinds of channels such as the sample channel, the body fluid-diluting liquid channel, the first diluent channel, the second diluent channel, the waste liquid channel, and the gas channel; and a pump tube 10, a channel-joining member 17, the mixer 15, and the gas-liquid separator 16 which are placed on the channels. At least a part of the sample channel is arranged on the channel-carrying substrate 19 of the embodiment according to the present invention. As explained hereinbefore, various kinds of channels used in the biological component-measuring device, such as the second, third and fourth portions 11d, 11e, 11o of sample channel (see FIG. 4), the first portion 11c of the body fluid-diluting liquid channel, the first and second portions 11i, 11j of the first diluent channel, the second diluent channel 11q, the waste liquid channel 11f, and the gas channel 11n; and a pump tube 10, the channel-joining member 17, the mixer 15, and the gas-liquid separator 16 which are placed on the channels, should be arranged on the channel-carrying substrate 19. See also FIGS. 4 and 5 concerning the reference numerals that denote channels and other elements.

The embodiment of the biological component-measuring device shown in FIG. 5 will be further described. A body fluid taken through the body fluid sampler 3a is diluted with a body fluid-diluting liquid supplied from the body fluid-diluting liquid tank 4a. The diluted body fluid is guided to the sensor 5 through the first, second and third portions 11a, 11d, 11e of the sample channel. While the diluted body fluid, or a sample, is flowing through the sample channel, a diluent and a gas from the gas channel are introduced into the third portion 11e of the sample channel. The sample and the diluent are mixed thoroughly by the mixer 15. The gas and an unnecessary amount of the diluted sample are discharged from the gas-liquid separator 16, and a proper amount of the diluted sample is guided to the sensor 5. After the completion of the measurement, the diluted sample is discharged from the sensor 5 through the waste liquid channel 11f to the waste liquid tank 6. When the calibration is carried out in place of the measurement, the sample channel and the sensor are flushed out with the flushing liquid in the flushing liquid tank 13 first. Then the first flow path changeover valve 9b and the second flow path changeover valve 9a are switched so that the calibrating liquid is introduced into the device, and the biological component-measuring device is calibrated. When a zero point calibration is carried out, only the diluent is introduced through the second diluent channel 11q to the sensor 5 and the indication of the sensor is checked. Another way of carrying out the zero point calibration is to supply the diluent in enough amount to the sensor, prior to the sampling of a body fluid, to fill the channels inside the sensor with the diluent, which provides a zero point calibration. Generally, the zero point varies very slightly during a measurement of a biological component. Therefore, in many cases, if the zero point calibration is done once prior to the measurement, it will not be necessary to carry out another zero point calibration until the measurement is completed. When a zero point calibration is not carried out during the measurement, the second diluent channel 11q and a flow path changeover valve for the switching to this channel may be omitted. Also, a flushing liquid may be utilized for zero point calibration. The flushing liquid normally does not include measured body fluid components. If the flushing pump is activated and the operation of removing clots in the sample channel is carried out while the biological component-measuring device is working, the flushing liquid flows into the sensor. If this flushing liquid is a liquid that does not include sugar, such as a physiological saline, or Ringer's solution, zero point calibration can be done in a state where the body fluid sampler 3a is connected to a living organism. For flushing the sensor may be used a calibrating liquid in place of a flushing liquid.

The ends of the channels arranged on the channel-carrying substrate 19 are designed so that the ends can be detachably connected to the corresponding channels, tanks, or equipment such as valves. When the channel-carrying substrate 19 is attached to the biological component-measuring device, these channels are connected with the corresponding elements. On the other hand, when the channel-carrying substrate 19 is detached from the device, the channels are also disconnected from the elements. The channel-carrying substrate 19 and the channels disposed on the substrate 19 can be easily and hygienically replaced with a new one when the examinee 2 is changed or there is an interval between the preceding measurement and the present measurement. The channel-carrying substrate 19 should be detached from the device in the following way, so that the leakage of a body fluid during the detachment will be prevented: The flushing liquid, the body fluid-diluting liquid, the calibrating liquid or the diluent is introduced into the elements on the substrate in which the sample remains, such as the sample channel, and such elements are washed with one of these liquids prior to the detachment. This channel-carrying substrate 19 is generally called "disposable channel-carrying substrate". Materials for the substrate and channels of such a disposable channel-carrying substrate should be inexpensive and easily available, because such disposable channel-carrying substrates usually are not used for a long time. Examples of the materials may include relatively inexpensive resins such as vinyl chloride, polyethylene, polypropylene, polystyrene, polyester, and nylon; and common rubbers such as natural rubber, butadiene rubber, isoprene rubber, and SBR. The other elements such as the sensor 5 and the pump 10d for sending the flushing liquid may be also disposed on the channel-carrying substrate 19. However, the fact that the substrate carrying such elements is thrown away raises the cost of a medical examination. An appropriate arrangement of such elements should be selected, with simplicity of the operation when the channel-carrying substrate is attached to the device, and hygienic care also taken into consideration.

The first portion 11i of the first diluent channel of the embodiment shown in FIG. 5 is equipped with a heater 15, which is an example of heating means for heating a diluent. The heater may be anything as long as it is capable of heating a diluent flowing through the first portion 11i of the first diluent channel. This heater 18 serves to control the temperature of the diluent, which eventually leads to the control of the temperature of the sample that is introduced into the sensor 5. The sensor 5 is controlled so as to have the same temperature as the living organism under examination, with the safety of the measurement considered. When a body fluid is taken from a human examinee, the temperature is usually set to 36 to 38 degrees Celsius. However, the temperature of the sample including the body fluid taken from the examinee often falls, affected by the temperature of the diluent and the atmospheric temperature while it is flowing through the channels. The effect of the atmospheric temperature is great, especially when it is low. A low temperature of the sample introduced into the sensor may change the sensitivity and precision of the sensor. There is also a probability that air bubbles may be emitted from the sample that sees a rapid increase in its temperature in the temperature-controlled sensor, which may disturb the measurement. A method to avoid such a failure is to keep the sample channel warm. However, the body fluid, especially blood, is apt to gel or deteriorate when it encounters a higher temperature than the temperature of the interior of the living organism. For example, there is a probability that blood of the human can gel when it is heated to 40 degrees Celsius or more. For this reason, a strict temperature control is required so that the temperature of the sample will not reach 40 degrees Celsius or more, when it is controlled by the warmed sample channel. On the other hand, the diluent, which does not include body fluids, will cause no problems when the temperature thereof is increased to a raised temperature of 50 degrees Celsius. Also, if the diluting ratio of the amount of the diluent to that of the sample is set to a large value, the temperature of the sample at the entrance of the sensor will be easily controlled by the temperature of the diluent. From this viewpoint, this embodiment of the biological component-measuring sensor is provided with the heater 18. Although the heater 18 is placed so that it warms the first portion 11i of the first diluent channel between the diluent tank 4b and the pump, it may be placed anywhere on the first diluent channel between the diluent tank 4b and the channel-joining member 17, for example a location downstream of the pump. Also, it is a good strategy to additionally warm the sample channel and the first diluent channel in order to control the temperature of the sample. However, care should be taken not to heat even apart of the sample excessively when the sample channel is kept warm.

The method of calibrating the biological component-measuring device according to the present invention is capable of calibrating not only the sensor, but also the entire device, including the channels and pumps, which is different from the conventional calibration of the biological component-measuring device. The calibration typically includes a zero point calibration carried out with a sample whose concentration of sugar, if the component measured is sugar, is zero, and a span calibration carried out for a sample whose concentration of sugar, if the component measured is sugar, is for example 200 mg/dL. A working curve is prepared from the two results and it serves for correction of measured values. Generally, variation in the measured value of the concentration used for the span calibration is large, while variation in the measured value in the zero point calibration is small. Although the zero point calibration may be omitted, it makes the calibration more accurate. With FIG. 5 referred to, the device is further provided with an additional channel, branched from the second diluent channel 11j, which, in turn, branched from the first portion 11i of the second diluent channel that connected with the second diluent tank 4b. Through the additional channel, the diluent is directly sent to the sensor 5 from the second diluent channel 11j. When the zero point calibration is carried out, only the diluent is supplied to the sensor 5. The diluent is appropriate to a liquid used for the zero point calibration because it does not include affecting components such as sugar. In the embodiment shown in FIG. 5, when the process moves on to the flushing step, which comes just before the calibration step, the zero point calibration of the sensor 5 may be commenced. Before the commencement, the flow path changeover valve placed just before the sensor 5 is switched to the state that the sensor communicates with the first diluent channel, from the state that the sensor communicates with the sample channel. Then, the diluent is allowed to flow for a predetermined time, for example, about one minute, and thus the zero calibration is done. If the zero point calibration is commenced at the same time as the flushing is begun, the time period necessary to carry out the entire step of the calibration can be reduced. If more than two known concentrations are used for the calibration, it will provide a more accurate calibration. In this method, span calibrations with several concentrations, as well as a zero point calibration, are carried out, and the working curve is prepared from the results. Naturally, the span calibrations with several concentrations provide a more precise working curve than the former calibration method described above. For the latter calibration method may be employed several calibrating liquid tanks 8, in which calibrating liquids in different concentrations are respectively stored. The calibrating liquids are introduced into the calibrating liquid channel one by one for the span calibrations. Alternatively, the ratio of the flow rate of the body fluid-diluting liquid or diluent to that of a single calibrating liquid may be changed, whereby calibrating liquids in different concentrations can be prepared for the span calibrations. When several calibrating liquid tanks 8 are prepared for the span calibrations, the cross valves for the first and second flow path changeover valves 9a, 9b may be replaced with four-way valves or six-way valves to switch the channels respectively communicating with the tanks.

Figure 7:
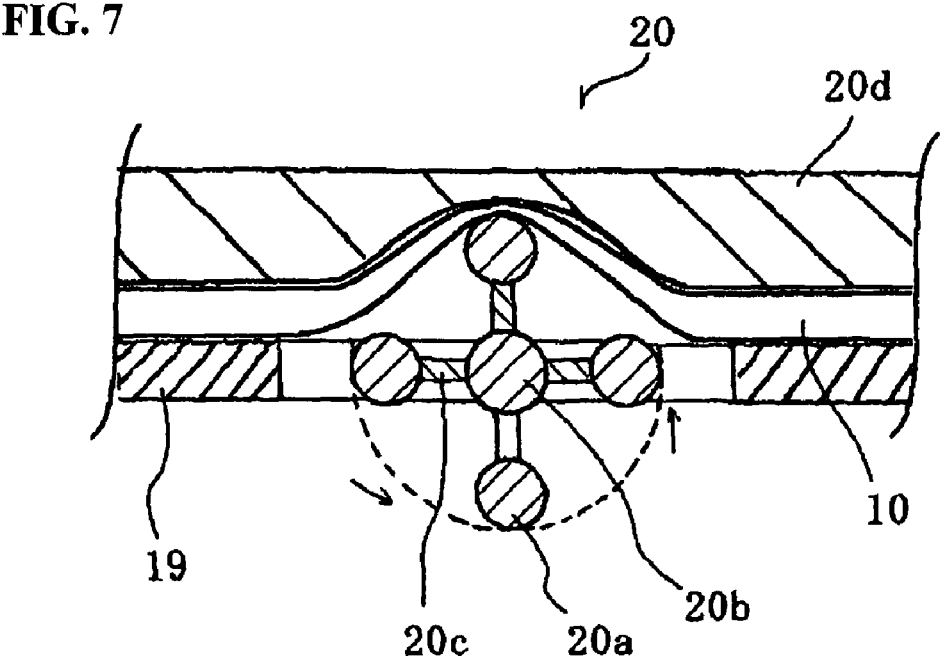
FIG. 7 is an illustration showing the structure of a tube pump.

Pumps, tubes for the pumps, and multipumps appropriate for the present invention will be explained. The pumps used in the biological component-measuring device according to the present invention may be pumps of any type as long as they are capable of transferring the respective liquids each in required amounts at predetermined discharges. Means for sending gas is also called a pump in this specification. Pumps called "tube pumps" or "peristaltic pumps", which are simple in their structures and can utilize tubes as the channels as they are, are appropriate for the pumps of the present invention. The pumps will be called "tube pumps" for convenience's sake. A typical tube pump has, as shown in FIG. 7, rollers 20a for squeezing elastic and flexible pump tubes 10, which function as the channels, sticks 20c for supporting these rollers 20a, a rotor 20b for supporting the sticks 20c connected thereto and rotating the rollers 20a, and a holding plate 20d, which tube pump provides the pump tubes with squeezing actions. The rotor 20b of tube pump rotates around the axis thereof, which, in turn, rotates the rollers 20a around the rotor 20b. The rotation of the rollers 20a squeezes the pump tubes 10. The rollers 20a hold the pump tubes 10 between the rollers and the holding plate 20d, and squeeze the pump tubes 10, thereby force the liquids in the pump tubes 10 out toward the downstream side in the tubes as the roller 20a rotate. The pump tubes 10, which are a part of the channels such as the second portion 11d of the sample channel, double as apart of the pump 10b. The pump tubes 10, which are a part of the tube pump 20 placed in the channels of various kinds arranged on the channel-carrying substrate 19, are also disposed on the same channel-carrying substrate 19. When the channel-carrying substrate 19 is attached to the biological component-measuring device and the device with the substrate is in use, the pump tubes 10, together with the roller 20a and the holding plate 20d, both of which belong to the biological component-measuring device, and between which the pump tubes 10 are sandwiched, form the tube pump 20.

The pump tubes 10 for the channels through which liquids are transferred are arranged parallel with each other on the channel-carrying substrate 19, which ensures that all the channels receive the squeezing force and the liquids in all the channels are forcibly transferred. Each of the rollers 20a of the tube pump 20 is made elongated ones, which are capable of squeezing all the pump tubes 10 simultaneously by a same roller 20a. Then, the flow rates of the respective liquids transferred through the channels are decided by the transverse sectional area of each pump tube 10 and the rotational speed of the rotor 20b. When the number of the rotor 20b is one, the flow velocity of the liquid in each channel is decided only by the transverse sectional area of the pump tube 10. In other words, the flow rate at which the liquid is transferred by the squeezing of the rollers 20a can be suitably decided by an adjustment to the inner diameter of the pump tube 10 in a channel. This type of tube is called "multipump". Multipumps have a simple structure and are capable of always keeping constant the ratio of the flow rate of one channel to that of another channel.

Figure 8:
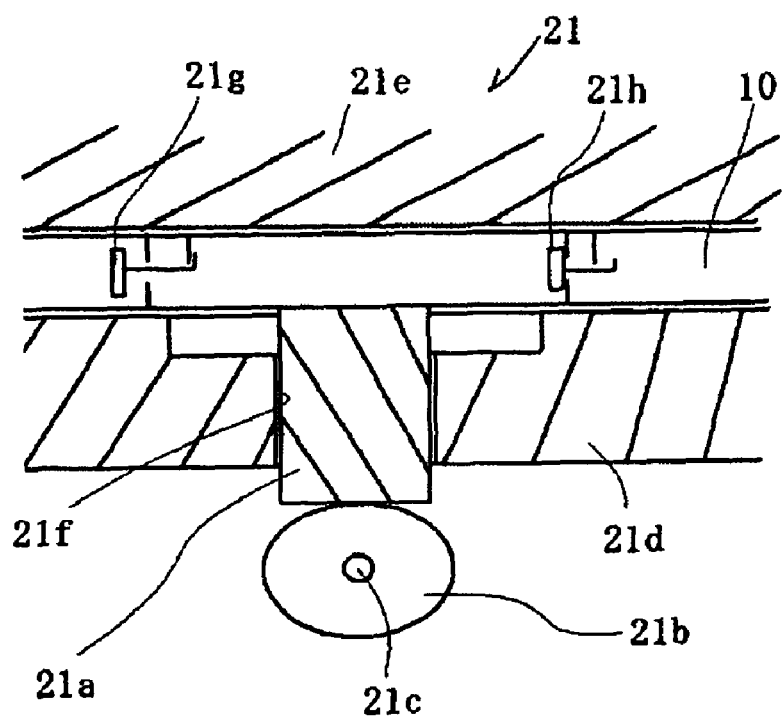
FIG. 8 is an illustration showing the structure of a pump.

Another example of the pump that has the same function as the tube pump 20 shown in FIG. 7 is a linear peristaltic pump. Another preferable type of pump, other than those with the squeezing function, may be a pump with a pressing function illustrated in FIG. 8. The pump 21 with a pressing function has, as shown in FIG. 8, a lower holding plate 21d and an upper holding plate 21e between which pump tubes 10 are sandwiched, a pressing member 21a capable of projecting from and sinking under the upper face of the lower holding plate 21d through a hole 21f pierced in the lower holding plate 21d, and an eccentric rotating cam 21b capable of rotating with keeping one end of the pressing member 21a contacted. When the eccentric rotating cam 21 rotates around its rotating shaft 21c, the pressing member 21a translates the rotation into such a vertical movement that the member projects from the upper face of the lower holding plate and sinks under it repeatedly through the hole 21f. On the other hand, the lower holding plate 21d may double as the channel-carrying substrate 19. Each of the fluid channels, such as a sample channel 11d, is provided with a first poppet valve 21g and a second poppet valve 21h inside the pump tube 10, which also serves as the channel. The upper holding plate 21e holds the elastic pump tube 10. The compression of the pump tube 10 by the pressing member 21a makes smaller the volume of the space inside the pump tube 10 delimited by the first poppet valve 21g and the second poppet valve 21h. As a result, the first poppet valve 21g is closed while the second poppet valve 21h is opened, which makes the fluid in the pump tube 10 flow out through the second poppet valve 21h. The pressing member 21a starts retracting after the volume of the space inside the pump tube 10 reaches the minimum. Then the elasticity of the pump tube 10 returns the volume to its maximum. In this state, the first poppet valve 21g becomes opened while the second poppet valve 21h becomes closed, which invites an inflow of the fluid into the delimited space of the tube pump 10 through the first poppet valve 21g. Through the repetition of this vertical movement, or the upward-and-downward movement of the pressing member 21a, the inflow of the fluid into the pump tube 10 and the outflow thereof from the tube are repeated alternately and the fluid is forcibly transferred through the channel. The pump in FIG. 8, in cooperation with the fluid channel that also serves as the pump tube 10, makes the fluid flow into and out of the pump tube 10 repeatedly.

Figure 11:
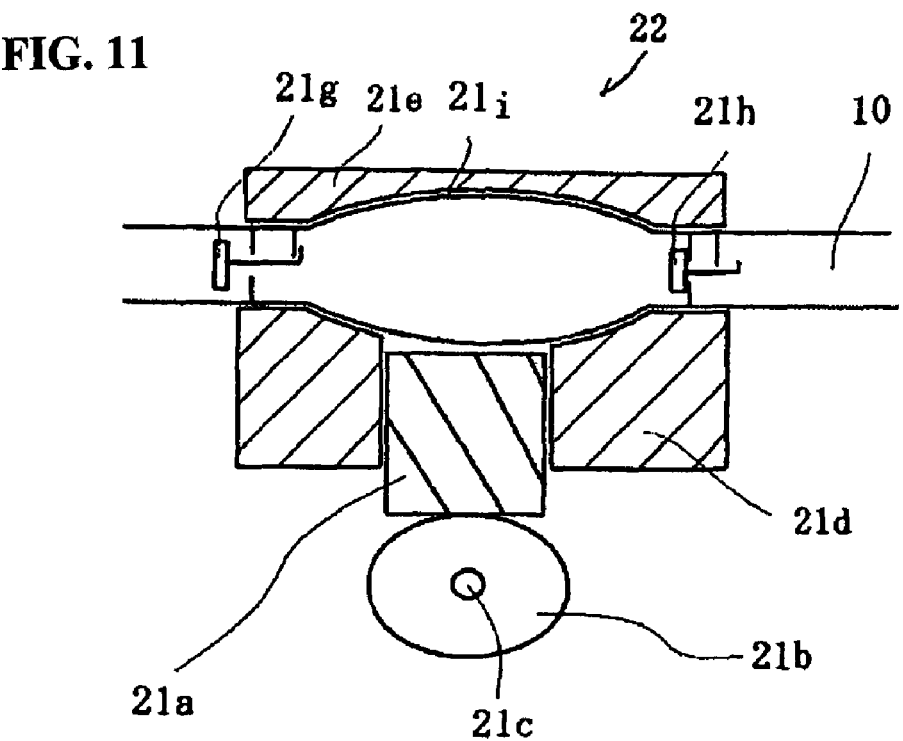
FIG. 11 is an illustration showing the structure of a pillow-type reciprocating pump.
Figure 12:
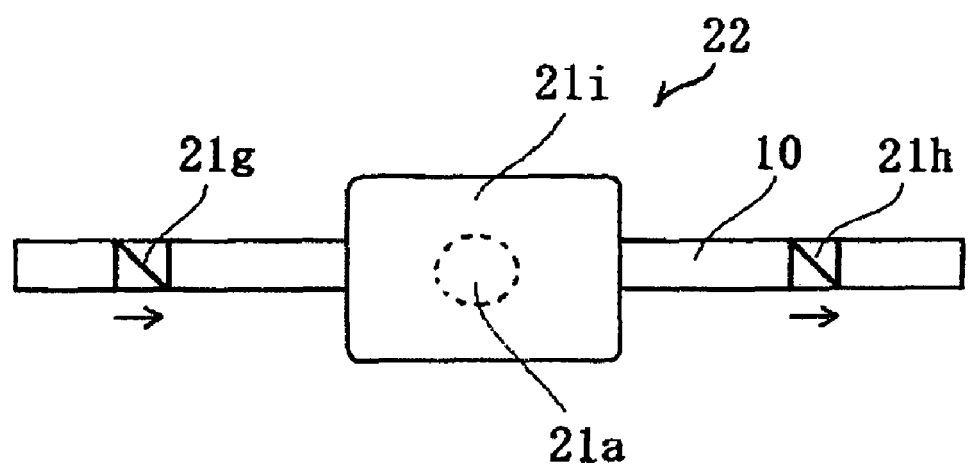
FIG. 12 is a top view illustration of the pillow-type reciprocating pump shown in FIG. 11, wherein a holding plate 21e is not shown.

The pump for sending a flushing liquid may be a part of the multipump explained above. However, one independent pump may be prepared for the pump for sending a flushing liquid, because the discharge of the pump is often larger than that of the other pumps, for example the pump for sending a sample. Appropriate examples of the pump for sending a flushing liquid may include tube pumps, linear peristaltic pumps, pumps shown in FIG. 8, diaphragm pumps, and so-called pillow-type reciprocating pumps as shown in FIGS. 11 and 12 which have a swollen tube in the pump shown in FIG. 8. These pumps should preferably be those with a function of preventing backflow.

There is no special limitation on the material of the channel-carrying substrate 19, as long as elements such as those various channels can be fixed to the substrate. In this embodiment is employed a hard synthetic resin. Soft and flexible synthetic resins may be used depending on the situations. Specific examples of the material for the channel-carrying substrate 19 are a sheet made of PVC, a hard film of hard PVC or PET, and a soft PVC to which PVC tubes are easily stuck. Although the channel-carrying substrate 19 may be produced by machining a raw material plate, the production by molding is preferable from the viewpoint of the price of the material, a reduction of waste material such as chips from the machining, and easiness of the mass production. For the molding should be used a method suitable for production in a medium or large quantity, such as compression molding or injection molding. The tubes may be fixed to the substrate by sticking them to predetermined locations on the substrate. Another method may be a die slide injection, often abbreviated to DSI, which is a precision molding by which the hollow tubes and the substrate are integrally molded. The DSI method does not require the sticking of the tubes after arranging them on the substrate. Still another method that may be utilized is fusible core injection molding in which tubes, each with a core inside it, are molded and the cores are melted away, whereby hollow tubes are prepared. The substrate 3 should preferably be made of an elastic soft material so that the substrate will have a certain dimensional tolerance. The channel-carrying substrate 19 may be attached to the mounting face of a biological component-measuring device 1 with pins and/or hooks. Channel-carrying substrates 19 especially made of such materials as resins with stretching properties can be attached to and detached from biological component-measuring devices 1 easily, and are preferably used.

The connection between each channel on the channel-carrying substrate 19 as shown in FIG. 5, which is a part of the biological component-measuring device, and the corresponding channel outside the substrate should preferably be made by a simple removable connector. For example, two channels to be connected with each other are formed from a soft material so as to have the shape of a tube, wherein one of the tubes has an inner diameter that is almost the same as the outer diameter of the other tube. Insertion of the latter tube into the former one makes the connection. Alternatively, two channels to be connected with each other may be formed from a soft material so as to have the shape of a tube, wherein both tubes have the same outer diameter. Another short tube with an inner diameter that is the same as the outer diameter of the tubes is prepared as a connector, and the respective ends of the two tubes, which are connected with each other, are inserted into the connector. A preferable example is a Luer connector often used to connect tubes made of flexible vinyl chloride. Tubes for the channels of the present invention are usually manufactured from the economical viewpoint because the tubes will be exchanged for new ones. Tubes made of flexible vinyl chloride are suitable for this purpose. Luer connectors made of flexible vinyl chloride or polycarbonate are easily connected with tubes of flexible vinyl chloride, and appropriate for the connector of the present invention also from the viewpoint of their production cost, a weak probability of leakage of the liquid in the tubes and connector, and a weak probability of slip-off of the tubes from the connector. A tube with an end portion, the outer face of which is in the shape of steps, the shape often called "bamboo sprout", wherein the outer diameter of the tube decreases stepwise toward its end, may serve as a simple connector appropriate for the present invention. The end of the tube is inserted into the inside of the other tube.

Figure 9:
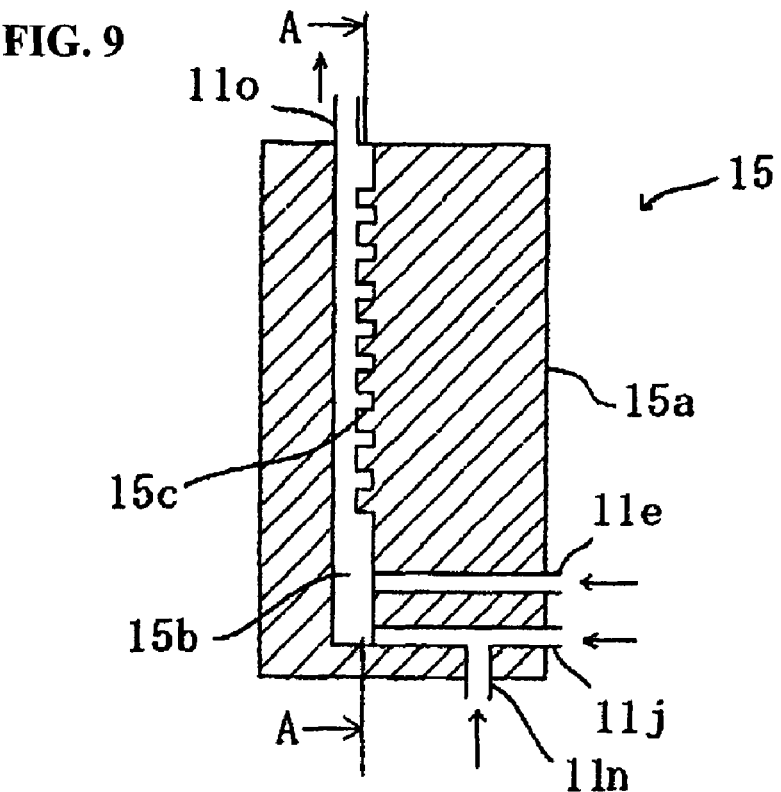
FIG. 9 is a sectional view showing the structure of a mixer.
Figure 10:
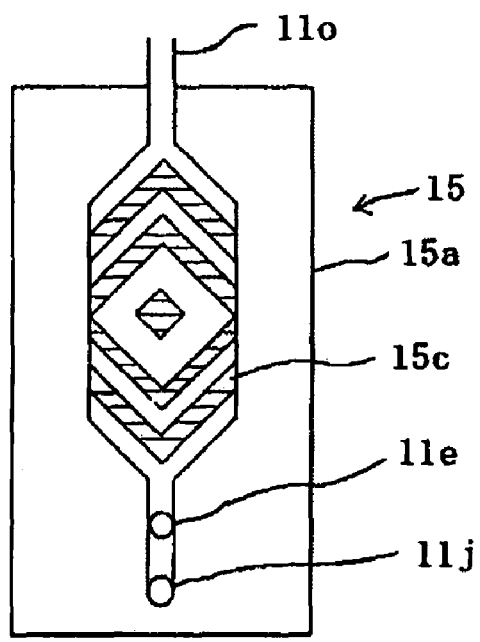
FIG. 10 is a sectional view showing the structure of a mixer, taken along a second line perpendicular to the first line along which the sectional view of FIG. 9 is taken.

For the mixer 15 various mechanical structures may be employed, as long as they are capable of mixing a sample transferred through the third portion 11e of the sample channel with a diluent, for example a buffer, supplied through the second portion 11j of the first diluent channel. Even a tube with a certain length may serve as the mixer. Because the forth portion 11o of the sample channel between the mixer 15 and the sensor 5 is short in the biological component-measuring device, mechanical structures capable of mixing a sample with the diluent sufficiently until the mixture reaches the sensor 5 should preferably be employed. An example of a preferable mixer 15 may be the one with the structure whose sectional view is shown in FIG. 9. The mixer 15 has a rugged part 15c comprised of continuous alternate projections and depressions running in the direction of fluid flow, which rugged part is formed in the inside face of a wall that defines, together with the other walls, an inner fluid flow space 15b of the mixer proper 15a in the shape of a rectangular parallelepiped. The inner fluid flow space 15b communicates with the third portion 11e of the sample channel, the second portion 11j of the first diluent channel, and the gas channel 11n at a lower part thereof, and with the fourth portion 11o of the sample channel at an upper part thereof. Another longitudinal sectional view of the mixer 15 is shown in FIG. 10, which is a view taken along line A-A in FIG. 9. In FIG. 10, the rugged part 15c has a central portion in the form of diamonds. In more detail, the rugged part 15c has, in the direction of fluid flow, a V-shaped rugged portion comprising alternate V-shaped projections and V-shaped depressions first. In other words, the first portion of the rugged part has several V-shaped projections and several V-shaped depressions each between adjacent V-shaped projections. Next comes the central portion, which is followed by a reverse V-shaped rugged portion comprised of several projections in the shaped of a reverse V and several reverse V-shaped depressions each between adjacent reverse V-shaped projections.

A sample and a diluent introduced into the inside of the mixer proper 15a strike against the first projection of the rugged part 15c, which disturbs the flow of the sample and that of the diluent. The disturbed flows of the sample and the diluent climb over the first projection and fall into the adjacent depression. In the depression the next projection makes the flow of the sample and that of the diluent collide, and the flows are disturbed again. Also, the flow of the sample and that of the diluent are divided into a flow component running straight and flow components each running aslant along the walls of the V, since the rugged part 15c has the V-shaped rugged portion and the reverse V-shaped rugged portion. This division of the flows also creates disturbed flows of the sample and the diluent. The repetition of the disturbances, caused by crashes of the sample and the diluent against the projections and the divisions of the flows into the straightly running components and the aslant running components, mixes the sample and the diluent.

In the explanation above, only a sample and a diluent are introduced into the mixer 15. However, the mixer is not limited to this embodiment. For example, a gas inert to samples and diluents, such as air or nitrogen gas, may be introduced into the inner fluid flow space 15b, to mix a sample and a diluent and to improve the efficiency of the mixing. A schematic block diagram of this embodiment is shown in FIG. 4. This embodiment further has a gas channel 11n, which, as well as the second portion 11d of the sample channel, is a flexible tube. The pump tube portion of the gas channel 11n is squeezed by the rollers, whereby a gas, such as air, in the channel is sent toward the mixer 15. The air is mixed with a diluent in the mixer 15 or upstream of the mixer 15, and a sample is further added. In this embodiment, a gas-liquid separator 16 is placed downstream of the mixer 15, and the liquid, which is a mixture of a sample and a diluent, and a gas are separated. The separated gas together with superfluous liquid is discharged through a gas-discharging channel 11p. Sending air to the mixer 15 in this way improves the efficiency of mixing a sample and a diluent. It also shortens the time period for which a sample is in the mixer 15 and the forth portion 11o of the sample channel, which makes it possible to measure a sampled body fluid quickly.

I claim:

1. A biological component-measuring system comprising:
    a biological component-measuring device; and
    a channel-carrying substrate, in which a sample including a body fluid taken by a body fluid sampler is transferred to a sensor through a sample channel by a pump and a biological component in the sample is measured by the sensor, the channel-carrying substrate including:
        a substrate detachably mountable on the biological component-measuring device;
        a sample channel connectable to the body fluid sampler and the sensor for measuring a biological component in the sample including the body fluid taken by the body fluid sampler, the sample channel fixed to the substrate so as to be capable of transferring the sample to the sensor by the pump; and
        a calibrating liquid channel connectable to a calibrating liquid tank, and connected to the sample channel at a location upstream of the pump via a first flow path changeover valve, the calibrating liquid channel fixed to the substrate so as to be capable of supplying a calibrating liquid stored in the calibrating liquid tank to the sample channel.

2. The biological component-measuring device according to claim 1, the substrate further comprising a body fluid-diluting liquid channel fixed thereto, connectable to a body fluid-diluting liquid tank, for supplying a body fluid-diluting liquid stored in the body fluid-diluting liquid tank to the body fluid sampler.

3. The biological component-measuring device according to claim 1, further comprising:
    a second flow path changeover valve placed in the body fluid-diluting liquid channel; and
    a second body fluid-diluting liquid channel, connected to the second flow path changeover valve, capable of mixing the body fluid-diluting liquid in the body fluid-diluting liquid channel with the calibrating liquid by a switching operation of the second flow path changeover valve.

4. The biological component-measuring device according to claim 1, the substrate further comprising a flushing liquid channel through which a flushing liquid flows, the flushing liquid channel connectable to a flushing liquid tank and connected with the sample channel at a location between the body fluid sampler and the first flow path changeover valve, and/or between the second flow path changeover valve and the body fluid sampler.

5. The method of calibrating the biological component-measuring device according to claim 4, comprising:
    a first operation of supplying a first portion of the flushing liquid at a first flow rate that is larger than a flow rate of the sample, to the sample channel from the flushing liquid channel while a biological component is being measured;
    a second operation of introducing the calibrating liquid into the sensor by a switching of the first flow path changeover valve placed in the sample channel, after the first portion of the flushing liquid is introduced into the sample channel and the sensor; and
    a third operation of introducing a second portion of the flushing liquid at a flow rate smaller than the first flow rate into the sample channel at a location upstream of the first flow path changeover valve and into the body fluid sampler during the second operation, to prevent the body fluid from flowing into the part filled with the second portion of the flushing liquid.

6. The biological component-measuring device according to claim 1, wherein the flushing liquid includes a predetermined concentration of biological components.

7. The biological component-measuring device according to claim 1, the substrate further provided with a first diluent channel through which a diluent for diluting the sample in the sample channel flows, the first diluent channel connectable to a diluent tank and connected with the sample channel at a location downstream of the first flow path changeover valve.

8. The biological component-measuring device according to claim 7, the substrate further provided with a gas channel connected to the first diluent channel or a junction of the first diluent channel and the sample channel.

9. The method of calibrating the biological component-measuring device according to claim 7, comprising:
 a first operation of carrying out a zero point calibration of the biological component-measuring device by supplying the diluent to the sample channel from the first diluent channel prior to sampling a biological component;
 a second operation of supplying the flushing liquid to the sample channel while the biological component is being measured; and
 a third operation of introducing the calibrating liquid in the calibrating liquid channel into the sensor via the sample channel by a switching of the first flow path changeover valve, without introducing the flushing liquid into the sensor.

10. The biological component-measuring device according to claim 1, wherein the calibrating liquid tank is placed at a lower level than the body fluid sampler.

* * * * *